(12) United States Patent  (10) Patent No.: US 7,471,394 B2
Padmanabhan et al.  (45) Date of Patent: Dec. 30, 2008

(54) OPTICAL DETECTION SYSTEM WITH POLARIZING BEAMSPLITTER

(75) Inventors: Aravind Padmanabhan, Plymouth, MN (US); Bernard S. Fritz, Eagan, MN (US)

(73) Assignee: Honeywell International Inc., Morristown, NJ (US)

( * ) Notice: Subject to any disclaimer, the term of this patent is extended or adjusted under 35 U.S.C. 154(b) by 265 days.

(21) Appl. No.: 11/027,134

(22) Filed: Dec. 30, 2004

(65) Prior Publication Data

US 2005/0118723 A1   Jun. 2, 2005

Related U.S. Application Data

(63) Continuation-in-part of application No. 10/304,773, filed on Nov. 26, 2002, which is a continuation-in-part of application No. 09/630,924, filed on Aug. 2, 2000, now Pat. No. 6,597,438.

(51) Int. Cl.
*G01J 4/00* (2006.01)
(52) U.S. Cl. ........................ 356/365; 356/246
(58) Field of Classification Search .......... 356/39, 356/436, 327, 339, 340, 365, 343, 243.2; 436/63, 10; 435/7.24
See application file for complete search history.

(56) References Cited

U.S. PATENT DOCUMENTS

| | | | |
|---|---|---|---|
| 2,407,731 A * | 9/1946 | Woodruff | 381/371 |
| 2,707,900 A * | 5/1955 | Maresh et al. | 356/246 |
| 3,316,412 A * | 4/1967 | Hirschberg | 250/226 |
| 3,612,689 A * | 10/1971 | Liskowitz | 356/342 |
| 3,822,095 A | 7/1974 | Hirschfeld | |
| 3,928,094 A | 12/1975 | Angell | |
| 3,976,862 A | 8/1976 | Curbelo | |

(Continued)

FOREIGN PATENT DOCUMENTS

DE   10122321   4/2002

(Continued)

OTHER PUBLICATIONS http://www.micronics.net/tsensor.htm, pp. 1-4, downloaded Jun. 14, 2000.

(Continued)

*Primary Examiner*—Tarifur Chowdhury
*Assistant Examiner*—Jonathon D Cook
(74) *Attorney, Agent, or Firm*—Kris T. Fredrick

(57) ABSTRACT

An optical detection system for use in flow cytometry or the like, which includes a polarizing beamsplitter 820 such as a Wollaston prism. A light source provides an input light beam to a flow stream, wherein the input light beam has a polarization direction. The particles in the flow stream may produce an output light beam that includes a polarized component and a depolarized component. The polarizing beamsplitter receives the output light beam, and provides a polarized light beam and a depolarized light beam to a pair of detectors. The pair of detectors provide a first output signal that corresponds to the polarized light beam and a second output signal that corresponds to the depolarized light beam. A controller or processor may use the first output signal and the second output signal to help identify/classify particles and/or particle characteristics in the flow stream.

30 Claims, 20 Drawing Sheets

U.S. PATENT DOCUMENTS

| | | | |
|---|---|---|---|
| 4,284,412 A | 8/1981 | Hansen et al. | |
| 4,478,076 A | 10/1984 | Bohrer | |
| 4,478,077 A | 10/1984 | Bohrer | |
| 4,501,144 A | 2/1985 | Higashi et al. | |
| 4,585,348 A * | 4/1986 | Chastang et al. | 356/369 |
| 4,599,000 A | 7/1986 | Yamada | |
| 4,651,564 A | 3/1987 | Johnson et al. | |
| 4,679,939 A * | 7/1987 | Curry et al. | 356/336 |
| 4,683,159 A | 7/1987 | Bohrer et al. | |
| 4,695,034 A | 9/1987 | Shimizu et al. | |
| 4,704,033 A | 11/1987 | Fay et al. | |
| 4,745,279 A | 5/1988 | Karkar et al. | |
| 4,818,263 A | 4/1989 | Mitch | |
| 4,874,949 A | 10/1989 | Harris et al. | |
| 4,906,094 A * | 3/1990 | Ashida | 356/336 |
| 4,911,616 A | 3/1990 | Laumann, Jr. | |
| 4,932,989 A | 6/1990 | Presby | |
| 5,017,497 A | 5/1991 | de Grooth et al. | |
| 5,050,429 A | 9/1991 | Nishimoto et al. | |
| 5,078,581 A | 1/1992 | Blum et al. | |
| 5,082,242 A | 1/1992 | Bonne et al. | |
| 5,085,562 A | 2/1992 | van Lintel | |
| 5,096,388 A | 3/1992 | Weinberg | |
| 5,108,623 A | 4/1992 | Cangelosi et al. | |
| 5,129,794 A | 7/1992 | Beatty | |
| 5,171,132 A | 12/1992 | Miyazaki et al. | |
| 5,176,358 A | 1/1993 | Bonne et al. | |
| 5,185,641 A | 2/1993 | Igushi et al. | |
| 5,194,909 A | 3/1993 | Tycko | |
| 5,219,278 A | 6/1993 | van Lintel | |
| 5,224,843 A | 7/1993 | van Lintel | |
| 5,244,537 A | 9/1993 | Ohnstein | |
| 5,323,999 A | 6/1994 | Bonne et al. | |
| 5,441,597 A | 8/1995 | Bonne et al. | |
| 5,452,878 A | 9/1995 | Gravesen et al. | |
| 5,457,526 A | 10/1995 | Kosaka | |
| 5,510,267 A | 4/1996 | Marshall | |
| 5,528,045 A | 6/1996 | Hoffman et al. | |
| 5,570,193 A | 10/1996 | Landa et al. | |
| 5,601,080 A | 2/1997 | Oppenheimer | |
| 5,616,501 A | 4/1997 | Rodriguez | |
| 5,633,724 A | 5/1997 | King et al. | |
| 5,637,881 A * | 6/1997 | Burghard et al. | 250/573 |
| 5,683,159 A | 11/1997 | Johnson | |
| 5,716,852 A | 2/1998 | Yager et al. | |
| 5,717,631 A | 2/1998 | Carley et al. | |
| 5,726,751 A | 3/1998 | Altendorf et al. | |
| 5,757,476 A | 5/1998 | Nakamoto et al. | |
| 5,760,900 A | 6/1998 | Ito et al. | |
| 5,793,485 A | 8/1998 | Gourley | |
| 5,799,030 A | 8/1998 | Brenner | |
| 5,822,170 A | 10/1998 | Cabuz et al. | |
| 5,836,750 A | 11/1998 | Cabuz | |
| 5,839,807 A | 11/1998 | Perlo | |
| 5,863,502 A | 1/1999 | Southgate et al. | |
| 5,867,266 A * | 2/1999 | Craighead | 356/344 |
| 5,880,474 A | 3/1999 | Norton et al. | |
| 5,893,722 A | 4/1999 | Hibbs-Brenner et al. | |
| 5,901,939 A | 5/1999 | Cabuz et al. | |
| 5,922,210 A | 7/1999 | Brody et al. | |
| 5,932,100 A | 8/1999 | Yager et al. | |
| 5,948,684 A | 9/1999 | Weigl et al. | |
| 5,970,315 A | 10/1999 | Carley et al. | |
| 5,971,158 A | 10/1999 | Yager et al. | |
| 5,972,710 A | 10/1999 | Weigl et al. | |
| 5,974,867 A | 11/1999 | Forster et al. | |
| 6,007,775 A | 12/1999 | Yager | |
| 6,032,689 A | 3/2000 | Tsai et al. | |
| 6,054,335 A | 4/2000 | Sun et al. | |
| 6,082,185 A | 7/2000 | Saaski | |
| 6,091,197 A | 7/2000 | Sun et al. | |
| 6,091,537 A | 7/2000 | Sun et al. | |
| 6,094,293 A | 7/2000 | Yokoyama et al. | |
| 6,097,485 A | 8/2000 | Lievan | |
| 6,097,859 A | 8/2000 | Solgaard et al. | |
| 6,106,245 A | 8/2000 | Cabuz | |
| 6,109,889 A | 8/2000 | Zengerie et al. | |
| 6,116,756 A | 9/2000 | Peeters et al. | |
| 6,124,663 A | 9/2000 | Haake et al. | |
| 6,139,800 A | 10/2000 | Chandler | |
| 6,179,586 B1 | 1/2001 | Herb et al. | |
| 6,184,607 B1 | 2/2001 | Cabuz et al. | |
| 6,215,221 B1 | 4/2001 | Cabuz et al. | |
| 6,237,619 B1 | 5/2001 | Maillefer et al. | |
| 6,240,944 B1 | 6/2001 | Ohnstein et al. | |
| 6,249,341 B1 | 6/2001 | Basiji et al. | |
| 6,281,975 B1 | 8/2001 | Munk | |
| 6,382,228 B1 | 5/2002 | Cabuz et al. | |
| 6,549,275 B1 | 4/2003 | Cabuz et al. | |
| 6,597,438 B1 | 7/2003 | Cabuz et al. | |
| 2002/0012168 A1 * | 1/2002 | Li | 359/487 |
| 2003/0142291 A1 | 7/2003 | Padmanabhan et al. | |
| 2003/0206349 A1 * | 11/2003 | Gage et al. | 359/495 |
| 2004/0224380 A1 * | 11/2004 | Chou et al. | 435/29 |

FOREIGN PATENT DOCUMENTS

| | | |
|---|---|---|
| EP | 0269076 | 6/1988 |
| EP | 1001326 | 5/1999 |
| EP | 1134548 | 9/2001 |
| JP | 61066947 | 4/1986 |
| JP | 10073528 | 8/1996 |
| JP | 2000056228 | 7/1999 |
| WO | WO 95/27199 | 3/1995 |
| WO | WO 99/60397 | 4/1999 |
| WO | WO 01/09598 | 2/2001 |
| WO | WO 02/10713 A2 | 2/2002 |
| WO | WO 02/10713 A3 | 2/2002 |
| WO | WO 02/10714 | 2/2002 |

OTHER PUBLICATIONS http://www.micronics.net/hfilter.htm, pp. 1-3, downloaded Jun. 14, 2000.

http://www.micronics.net/mcytometry.htm, pp. 1-4, downloaded Jun. 14, 2000.

http://www.micronics.net/orcafluidics.htm, pp. 1-4, downloaded Jun. 14, 2000.

Altendorf et al, "Results Obtained Using A Prototype Microfluidics-Based Hematology Analyzer", SPIE Biomedical Optics 97, 1997.

Altendorf et al., "Differential Blood Cell Counts Obtained Using A Microchannel Based Flow Cytometer", Solid State Sensors & Actuators, vol. 1, 531, 1997.

Altendorf et al., "Implementation Of Novel Optical Detection Methods For Clinically Important Blood Analytes Using Microfabricated Flow Structures (T-Sensors™)", MicroTAS 98, Banff, Canada, Apr. 1998.

Altendorf et al., "Microfabrication Technology For Research And Diagnostics, Silicon Microchannel Optical Flow Cytometry", SPIE Proceedings, Biomedical Optics 96, Jan. 1996.

Cabuz et al., "Mesoscopic Sampler Based on 3D Array of Electrostatically Activated Diaphragms", The 10th Int. Conf. On Solid-State Sensors and Actuators, Transducers'99, Jun. 7-12, 1999, Sendai Japan, p. 1890-1.

Darling et al., "Integration Of Microeletrodes With Etched Microchannels For In-Stream Electrochemical Analysis", MicroTAS 98, Banff, Canada, Apr. 1998.

Fedder et al., "Laminated High-Aspect-Ratio Microstructures in a Conventional CMOS Process", Proc. Micro Electro Mechanical Systems Workshop, MEMS 96, San Diego, California, Feb. 11-15, 1996, pp. 13-18.

Hatch et al., "Microfluidic Approaches To Immunoassays", SPIE conference on Micromachining and Microfabrication Symposium at Santa Clara, CA, Sep. 20-22, 1999.

Huang et al., "Development Of A Flow Cytometry Based Miniature Chemical Fluid Analysis System Using Fluorescent Microbeads", SPIE Biomedical Optics, BIOS 97, conference proceedings, 1997.

Lehman et al., "High-Frequency Modulation Characteristics of Red VCSELs", Electronics Letters, Feb. 13, 1997, vol. 33(4), pp. 298-300. Copyright 1997 IEE.

Ohnstein et al., "Micromachined Silicon Microvalve", Proceedings of MEMS, 1990, IEEE Micro Electromechanical Systems, Napa Valley, California, Feb. 11-14, 1990, pp. 95-98.

Roulet et al., "Fabrication of Multilayer Systems Combining Microfluidic and Microoptical Elements for Fluorescence Detection," Journal of Microelectromechanical Systems, vol. 10 No. 44, pp. 483-491, Dec. 4, 2001.

Shapiro, "Practical Flow Cytometry", third edition, 1995, p. 237.

Strzelecka et al., "Parallel Free-Space Optical Interconnect Based on Arrays of Vertical-Cavity Lasers and Detectors with Monolithic Microlenses", Applied Optics, v. 37(14), May 10, 1998, pp. 2811-2821. Copyright 1998 Optical Society of America.

Terstappen et al., "Four-Parameter White Blood Cell Differential Counting Based on Light Scattering Measurements", Alan R. Liss, Inc., Cytometery 9:39-43, 1988.

Toshiyoshi et al., "Micromechanical Lens Scanner for Fiber Optic Switches", Proc. 3$^{rd}$ International Conference on Micro Opto Electro Mechanical Systems (MOEMS 99), Aug. 30-Sep. 1, 1999, Mainz, Germany, pp. 165-170.

Toshiyoshi et al., "Surface micromachined 2D Lens Scanner Array", Proc. IEEE?LEOS International Coference on Optical EMMS/ Sheraton Kauai Resort, Kauai, Hawaii, Aug. 21-24, 2000, 2 pages.

Tuantranont et al., "Flip Chip Integration of Lenslet Arrays on Segmented Deformable Micromirrors", Part of the Symposium on Design, Test and Microfabrication of MEMS and MOEMS, Paris, France, Mar.-Apr. 1999, SPIE vol. 3680, 0277-786X/99, pp. 668-678.

Tuantranont et al., "MEMS-Controllable Microlens Array For Beam Steering and Precision Alignment in Optical Interconnect Systems", Solid-State Sensor and Actuator Workshop, Hilton Head Island, South Carolina, Jun. 4-8, 2000, pp. 101-104.

Weigh et al., "Silicon-Microfabricated Diffusion-Based Optical Chemical Sensor", Reprint from "Sensors & Actuators" B 38-39, 452-457, 1997.

Weigl et al., "Microfluidic Diffusion-Based Separation And Detection", Science, vol. 283, pp. 346-347, Jan. 15, 1999.

Weigl et al., "Optical And Electrochemical Diffusion-Based Detection Of Analytes In Complex Samples Using Microfabricated Flow Structures (T-SensorSTM)", Micro- and nanofabn'cated electro-optical mechanical systems for biomedical and environmental applications II- SPIE vol. 3606, Jan. 25-26, 1999.

Weigl et al., "Simultaneous Self-Referencing Analyte Determination In Complex Sample Solutions Using Microfabricated Flow Structures (T-Sensors™)", Proceedings of MicroTAS 98, 81-4, Banff, Canada, 1998.

Weigl et al., "Diffusion-Based Optical Chemical Detection In Silicon Flow Structures", B. Weigl et al., Analytical Methods & Instrumentation, µTTAS 96 special edition, 1996.

Weigl et al., "Fluorescence And Absorbance Analyte Sensing In Whole Blood And Plasma Based On Diffusion Separation In Silicon-Microfabricated Flow Structures (T-Sensors™)", Biomedical Optics, vol. 6, No. 1, Jul. 1997.

Weigl et al., "Rapid Sequential Chemical Analysis Using Multiple Fluorescent Reporter Beads"µTTAS 96 Conference Proceedings, 1996.

Weigl, "Microfluidic Diffusion Based Electrochemical Detection Using Microfabricated Flow Structures (T-Sensors™)", Analytical Chemistry, submitted 1999.

Weigl, "Whole Blood Assays Using Microfluidics-Based T-SensorsSTm Technology", Medical Design Online, http://news.medicaldesignonline.com/featuresarticles/19990416-5922.html, Apr. 1999.

Yager et al., "Applying Microfluidic Chemical Analytical Systems To Imperfect Samples", Micro Total Analysis Systems 98, D. Harrison & A. van den Berg (ed.), Kluwer Academic Publishers, Dordrecht, 207-212, 1998.

Yager et al., "Design Of Microfluidic Sample Preconditioning Systems For Detection Of Biological Agents In Environmental Samples", Yager, M. et al., SPIE Proceedings, 3515, 252-259, 1998.

* cited by examiner

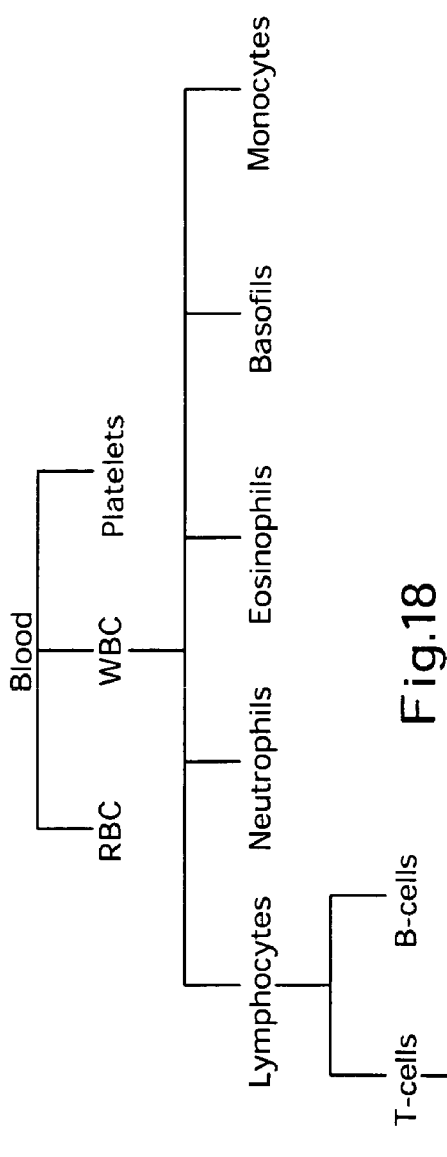
Fig.18
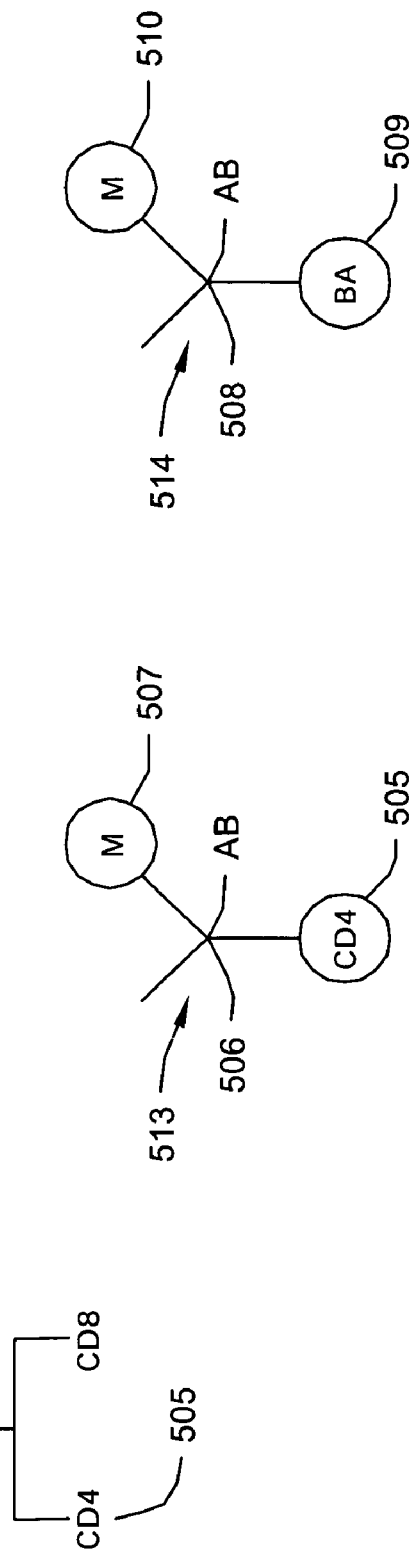
Fig.19a
Fig.19b

OPTICAL DETECTION SYSTEM WITH POLARIZING BEAMSPLITTER The present patent application claims priority as a continuation-in-part of co-pending U.S. Nonprovisional patent application Ser. No. 10/304,773, filed Nov. 26, 2002, and entitled "Portable Scattering and Fluorescence Cytometer", which is a continuation-in-part of U.S. Nonprovisional patent application Ser. No. 09/630,924, filed Aug. 2, 2000, now U.S. Pat. No. 6,597,438 and entitled "Portable Flow Cytometer", both of which are incorporated herein by reference.

BACKGROUND

The present invention relates generally to flow cytometers. More particularly, the present invention relates to portable flow cytometers that sense optical properties of microscopic biological particles or components in a flow stream.

Flow cytometry is a technique that is used to determine certain physical and chemical properties of microscopic biological particles or components by sensing certain optical properties of the particles or components. To do so, for instance, the particles are arranged in single file using hydrodynamic focusing within a sheath fluid. The particles are then individually interrogated by a light beam. Each particle scatters the light beam and produces a scatter profile. The scatter profile is often identified by measuring the light intensity at different scatter angles. Certain physical and/or chemical properties of each particle can then be determined from the scatter profile.

Flow cytometry is currently used in a wide variety of applications including hematology, immunology, genetics, food science, pharmacology, microbiology, parasitology and oncology, to name a few. A limitation of many commercially available flow cytometer systems is that they are relatively large bench top instruments that must remain in a central laboratory environment. Accordingly, the use of such flow cytometers is often not available in remote locations or for continuous hematological monitoring.

SUMMARY

The present invention overcomes many of the disadvantages of the prior art by providing a highly miniaturized portable and wearable cytometer that can be used at remote locations, such as at home or in the field. Such a flow cytometer may help improve healthcare of patients by providing detailed individual hematological evaluation and uncovering statistical trends. By detecting an infection early, the infection may be more readily treatable.

In military applications, the portable miniaturized cytometer of the present invention may help save lives by providing early detection of infection due to biological agents. It is known that expanded activity in the biological sciences has increased the probability of accidental exposure to dangerous biological agents. The ease of manufacturing such agents also raises a serious threat to their use by terrorists, regional powers or developing third world nations. The lack of safeguards in international agreements outlawing biological warfare, and compelling evidence that those agreements may have been violated, reinforces the need for a strong capability for biological defense. Pre-exposure detection of pathogen agents, as well as post-exposure detection of incipient infections may be used cooperatively to ensure efficient protection during biological warfare.

As part of the body's natural defense against antigens, the white blood cell count increases at the onset of infection. There are several types of white blood cells including neutrophils, lymphocytes, monocytes, eosinophils and basofils. Lymphocytes create antibodies that attack the invaders and mark them for destruction by the neutrophils and macrophages. In an individual without chronic diseases (such as tuberculosis or cancer), an increase in the percentage of lymphocytes in the overall white cell count is an indication of a viral infection. On the other side, an increase in the percentage of the neutrophils is an indication of a developing bacterial infection. Through counting of neutrophils and lymphocytes, a clear infection warning can be issued with differentiation between viral or bacterial causes.

The first clinical symptoms of infection from some bacterial agents such as bacillus anthrax appear after one to six days. In 99% of the cases, patients showing symptoms from anthrax cannot be treated, and will most likely die. However, if treatment is given before the first symptoms appear, most patients can be successfully treated. Accordingly, it would be highly desirable to provide an early alert and potential therapeutic intervention for hematologic abnormalities before symptoms occur. In many cases, such an early alert and treatment may greatly improve the outcome for many patients.

In an illustrative example of the present invention, a portable miniaturized cytometer is provided for identifying and/or counting selected particles in a fluid sample such as a blood sample. One illustrative miniaturized portable cytometer includes a fluid receiver for receiving the fluid sample. One or more reservoirs are provided for storing supporting fluids such as lyse and sheath fluids. For many commercial flow cytometer systems, a precision fluid driving system is used for providing precise pressures to the fluids. A limitation of this approach is that precision fluid driving systems can be bulky, complex and may require significant power.

To avoid many of these limitations, an illustrative example uses a non-precision fluid driver that is controlled by a closed loop feedback path. The non-precision fluid driver is coupled to the fluid receiver and the various supporting fluid reservoirs, and applies separate pressures to the sample fluid and the supporting fluids. To control the velocity of the sample fluid and the supporting fluids, one or more valves are coupled to the fluid driver. The valves are used to regulate the non-precision pressures that are applied to the sample fluid and the supporting fluids by the non-precision fluid driver.

To complete the feedback loop, flow sensors are provided downstream of the fluid driver to measure the fluid velocity of the sample fluid and the supporting fluids. A controller or processor receives the signals from the flow sensors, and adjusts the appropriate valves so that the desired fluid velocities of the sample fluid and supporting fluids are achieved. The flow sensors may be thermal anemometer type flow sensors.

In one illustrative example, the non-precision fluid driver is manually powered. A manually powered fluid driver may include, for example, a bulb with check valve or a plunger. In either case, the manually generated pressure may be provided to a first pressure chamber. A first valve is then provided for controllably releasing the pressure in the first pressure chamber to a second pressure chamber. A second valve may be provided in the second pressure chamber for controllably venting the pressure in the second pressure chamber. The controller opens the first valve when the fluid flow in the downstream fluid stream drops below a first predetermined value and opens the second valve when the fluid flow in the downstream fluid stream increases above a second predetermined value. Each valve may be an array of electrostatically actuated microvalves that are individually addressable and controllable.

The controlled sample fluid and supporting fluids are provided to a fluidic circuit. The fluidic circuit performs hydrodynamic focusing, which causes the desired particles to fall into single file along a core stream surrounded by a sheath fluid. One or more light sources or light source arrangements provide light through the flow stream, and one or more light detectors or light detector arrangements detect the scatter profile and fluorescence of the particles in the flow stream. An arrangement may have one or more light sources and/or one or more light detectors. An arrangement may include a single optical device or element or an array of such items. A processing block uses the output signals from the light detectors to identify and/or count selected particles in the core stream.

The miniaturized portable cytometer may be provided in a housing sufficiently small to be appropriately and comfortably "wearable" on a person. In one illustrative example of the invention, the housing is sized similar to a wrist watch. The wearable housing may include, for example, a base, a cover, and a hinge that secures the base to the cover. The non-precision fluid driver and regulating valves may be incorporated into the cover, while the fluid reservoirs, flow sensors and fluidic circuit may be incorporated into a removable cartridge that is inserted into the housing. The fluidic circuit may dilute the blood sample, perform red cell lysing, and perform hydrodynamic focusing for flow and core stream formation, if desired. The light sources may be situated in either the base or the cover, and aligned with the flow stream of the removable cartridge. The light detectors may be provided generally opposite to the light sources. The processor and batteries may be provided in either the base or the cover of the housing, as desired.

The light source may include one or a linear array of first light sources along a first light source axis. The first light source axis may be rotated relative to the central axis of the flow stream. A lens may be provided adjacent each light source to focus the light at the particles in the core stream. A detector or set of light detectors may then be placed in-line with the light source or each of the light sources. Such an arrangement can be used to determine, for example, the alignment and width of the core stream within the flow stream. If the core stream of particles is not in proper alignment, the controller can adjust the fluid velocity of the sample fluid or one of the supporting fluids to bring the core stream into alignment. The light detector or set of light detectors may also be used to detect the velocity and size of each particle, as well as the number of particles.

Another light source or set of the light sources may be provided along second light source axis. A lens may be provided adjacent each light source to focus the light at the particles in the core stream. A second detector or set of light detectors may then be placed on either side of the in-line position of each light source for measuring the small angle scattering (SALS) produced by selected particles in the flow stream.

The second light source or set of light sources may also be used in conjunction with the first set of light sources to determine the time-of-flight or velocity of the particles in the flow stream. By knowing the velocity of the particles, small variations in the flow rate caused by the fluid driver can be minimized or removed by the controller.

A third light source or set of light sources may be provided along a third light source axis. A lens may be provided adjacent each light source to provide collimated light to the flow stream. An annular light detector or detectors may then be placed opposite the light source or light sources for measuring the forward angle scattering (FALS) produced by the selected particles in the flow stream. Each of the first, second and third light sources or sets of light sources may include an array of lasers such as vertical cavity surface emitting lasers (VCSELs) fabricated on a common substrate. Each of the first, second and third detectors or sets of light detectors may include a photo detector or an array of photo detectors such as p-i-n photodiodes, GaAs photodiodes with integrated FET circuits, resonant cavity photo detectors (RCPDs), or any other suitable light detectors.

The selected particles may be, for example, neutrophils and/or lymphocytes white blood cells. By examining the scatter profile of each particle, the miniaturized portable cytometer of the present invention may identify and/or counts the neutrophils and lymphocytes in a blood sample, and provide a clear infection warning with differentiation between viral and bacterial causes.

In some embodiments, fluorescence is used to further identify and analyze various white cells. Antibodies may be associated with particular white blood cells. The antibodies have markers or tags attached to them. These white blood cells may be impinged with light which causes their associated markers or tags to fluoresce and emit light. The light may be collected, filtered as needed, and directed to one or more photo detectors. This detection may be used to identify and monitor specific subclasses of white cells and blood-based proteins, among other things.

In yet another embodiment, an optical detection system is provided that includes a light source for providing an input light beam to a flow stream, wherein the input light beam has a polarization direction. A polarizing beamsplitter is provided for receiving the output light beam from the flow stream, and for providing a polarized light beam and a depolarized light beam. The polarizing beamsplitter may be, for example, a Wollaston prism in cube or film form. A light receiving element, such as a pair of photodetectors, may be provided for receiving the polarized light beam and the depolarized light beam, and for providing a first output signal that corresponds to the polarized light beam and a second output signal that corresponds to the depolarized light beam. A controller or processor may use the first output signal and the second output signal to help identify/classify particles and/or particle characteristics in the flow stream.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 18 is a diagram of the blood hierarchy emphasizing an area of cytometer application;

FIGS. 19a and 19b show the antibody and marker structure associated with the cell or bacteria of interest;

DESCRIPTION

Figure 1:
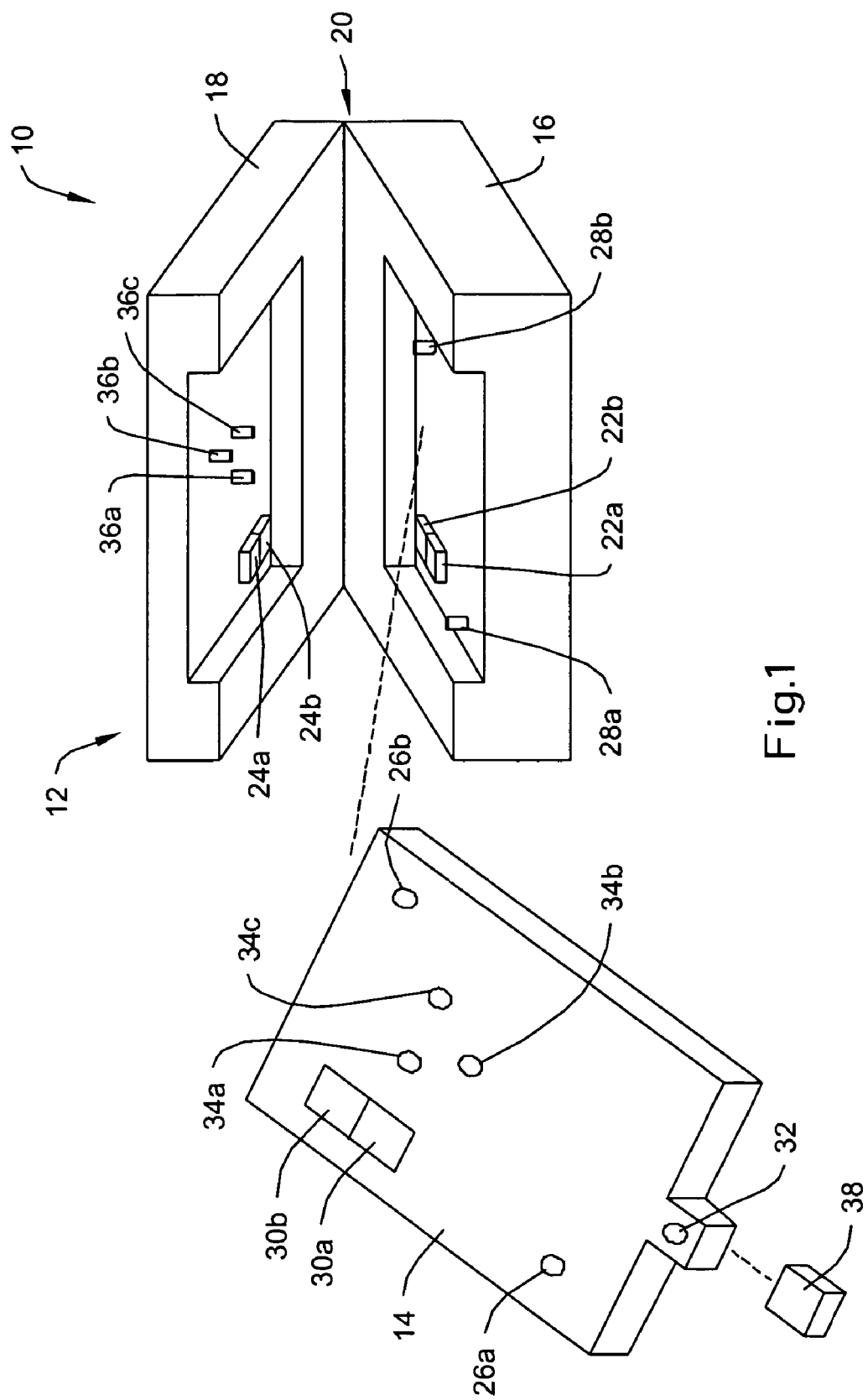
FIG. 1 is a perspective view of an illustrative portable cytometer in accordance with the present invention.

FIG. 1 is a perspective view of an illustrative miniaturized portable cytometer in accordance with the present invention. The cytometer is generally shown at 10, and includes a housing 12 and a removable or replaceable cartridge 14. The illustrative housing 12 includes a base 16, a cover 18, and a hinge 20 that attaches the base 16 to the cover 18. The base 16 includes light sources 22a and 22b, associated optics and the necessary electronics for operation of the cytometer. The cover 12 includes a manual pressurizing element, pressure-chambers with control microvalves, and light detectors 24a and 24b with associated optics.

The removable cartridge 14 may receive a sample fluid via a sample collector port 32. A cap 38 may be used to protect the sample collector port 32 when the removable cartridge 14 is not in use. The removable cartridge 14 may perform blood dilution, red cell lysing, and/or hydrodynamic focusing for core formation. The removable cartridge 14 may be constructed similar to the fluidic circuits available from Micronics Technologies, some of which are fabricated using a laminated structure with etched channels.

The removable structure or cartridge 14 is inserted into the housing when the cover 18 is in the open position. The removable cartridge 14 may include holes 26a and 26b for receiving registration pins 28a and 28b in the base 16, which help provide alignment and coupling between the different parts of the instrument. The removable cartridge 14 also may include transparent flow stream windows 30a and 30b, which may be in alignment with the arrays of the light sources 22a and 22b, and light detectors 24a and 24b. When the cover is moved to the closed position, and the system is pressurized, the cover 18 provides controlled pressures to pressure receiving ports 34a, 34b, and 34c in the removable cartridge 14 via pressure providing ports 36a, 36b and 36c, respectively.

To initiate a test, the cover 18 is lifted and a new cartridge 14 is placed and registered onto the base 16. A blood sample is introduced into the sample collector 32. The cover 18 is closed and the system is manually pressurized. Once pressurized, the instrument performs a white blood cell cytometry measurement. The removable cartridge 14 provides blood dilution, red cell lysing, and hydrodynamic focusing for core formation. The light sources 22a and 22b, light detectors 24a and 24b and associated control and processing electronics perform differentiation and counting of white blood cells based on light scattering fluorescent signals. Rather than using a hinged construction for the housing 12, it is contemplated that a sliding cartridge slot or any other suitable construction may be used.

Figure 2:
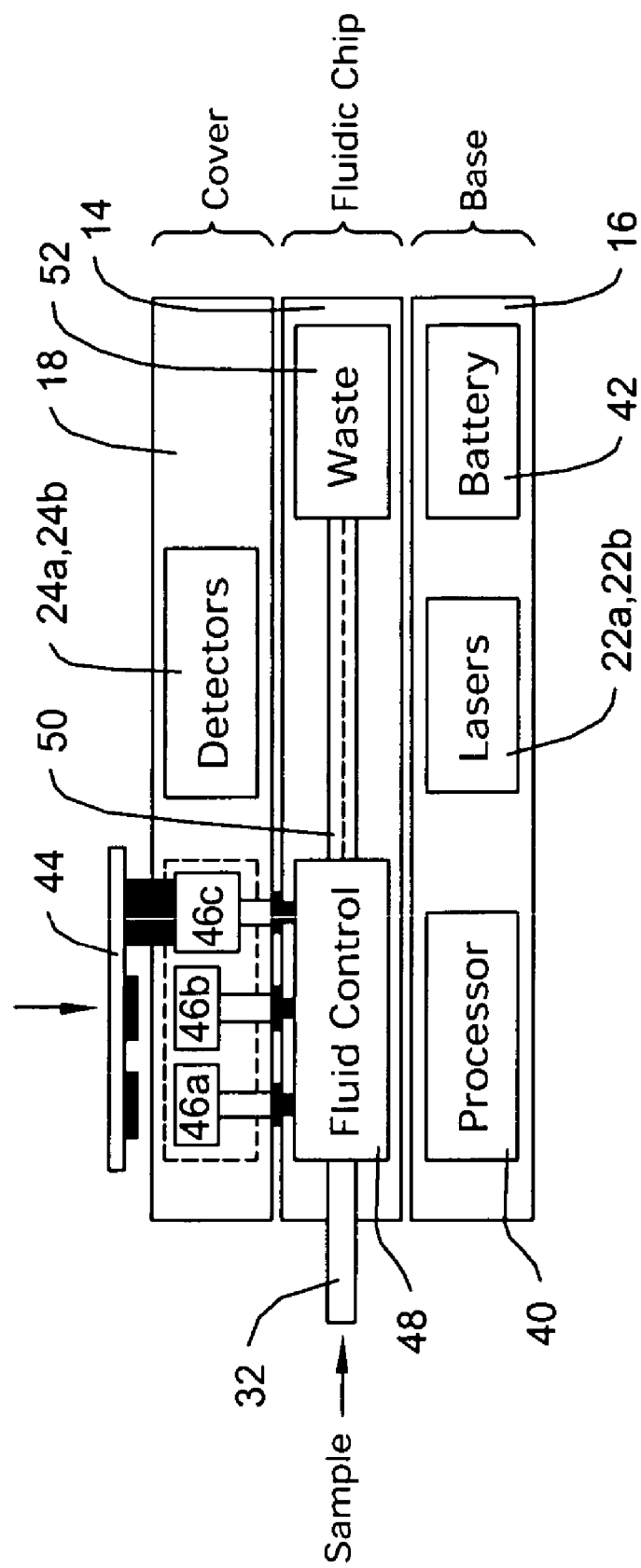
FIG. 2 is a schematic view of the illustrative portable cytometer of FIG. 1.

FIG. 2 is a schematic view of the illustrative cytometer of FIG. 1. As above, the base 16 may include light sources 22a and 22b, associated optics and the necessary control and processing electronics 40 for operation of the cytometer. The base 16 may also include a battery 42 for powering the cytometer. The cover 12 is shown having a manual pressurizing element 44, pressure-chambers 46a, 46b and 46c with control microvalves, and light detectors 24a and 24b with associated optics.

The removable cartridge 14 may receive a sample fluid via the sample collector port 32. When pressurized by the cover 18, the removable cartridge 14 performs blood dilution, red cell lysing, and hydrodynamic focusing for core formation in the present device. Once formed, the core is provided down a flow stream path 50, which passes the flow stream windows 30a and 30b of FIG. 1. The light sources 22a and 22b, and associated optics in the base provide light through and to the core stream via the flow stream windows 30a and 30b. The light detectors 24a and 24b, and associated optics receive scattered and non-scattered light from the core, also via the flow stream windows 30a and 30b, respectively. The controller or processor 40 receives output signals from the detectors 24a and 24b, and differentiates, identifies and counts selected white blood cells that are present in the core stream.

It is contemplated that the removable cartridge 14 may include a fluid control block 48 for helping control the velocity of each of the fluids. In the illustrative example, the fluid control block 48 includes flow sensors for sensing the velocity of the various fluids and reports the velocities to the controller or processor 40. The controller or processor 40 may then adjust the microvalves associated with pressure-chambers 46a, 46b and 46c to achieve the desired pressures and thus desired fluid velocities for proper operation of the cytometer.

Because blood and other biological waste can spread disease, the removable cartridge 14 may have a waste reservoir 52 downstream of the flow stream windows 30a and 30b. The waste reservoir 52 may receive and store the fluid of the flow stream in the removable cartridge 14. When a test is completed, the removable cartridge may be removed and disposed of, preferably in a container compatible with biological waste.

Figure 3:
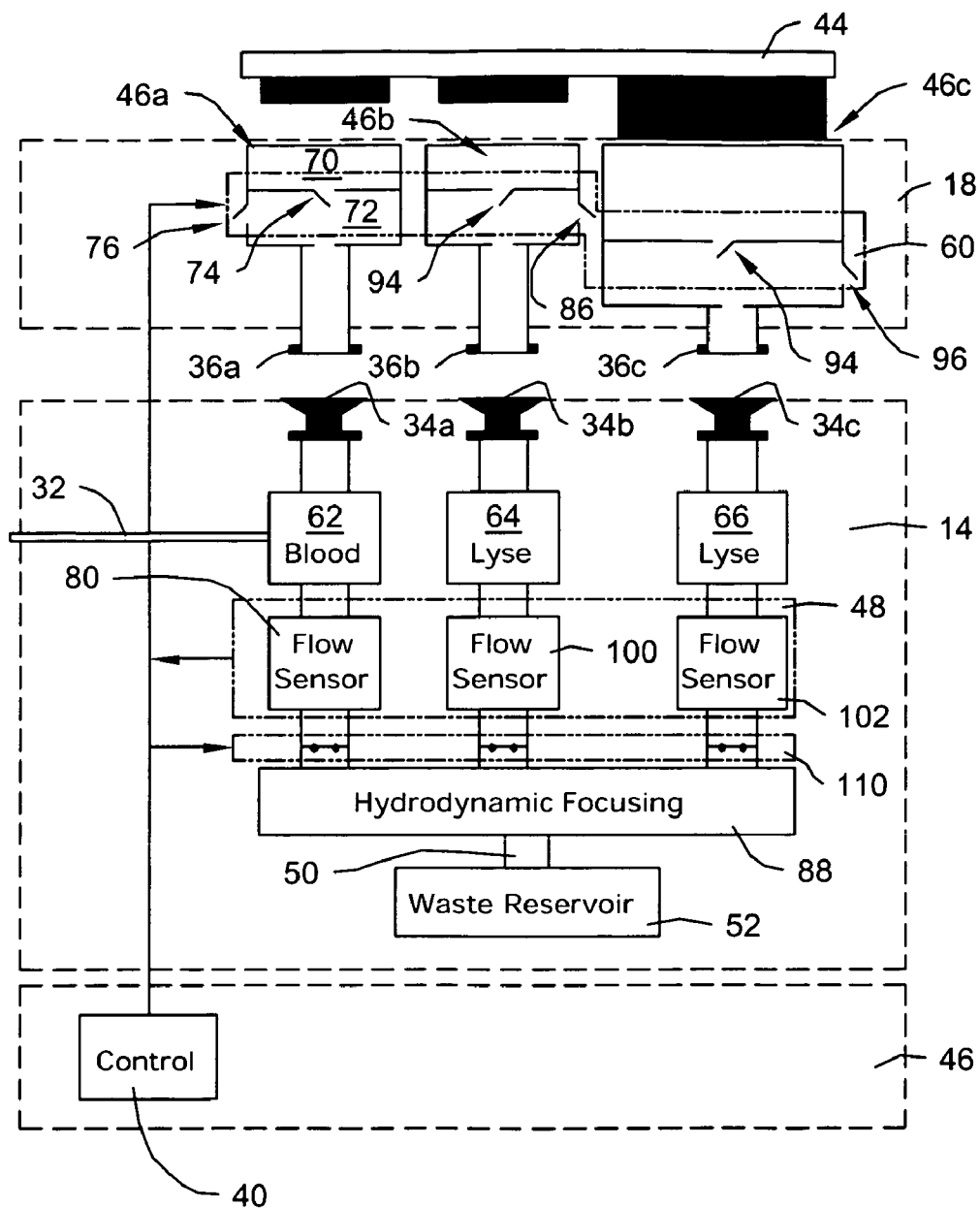
FIG. 3 is a more detailed schematic diagram showing the cytometer of FIG. 2 with the cover not yet depressed.
Figure 4:
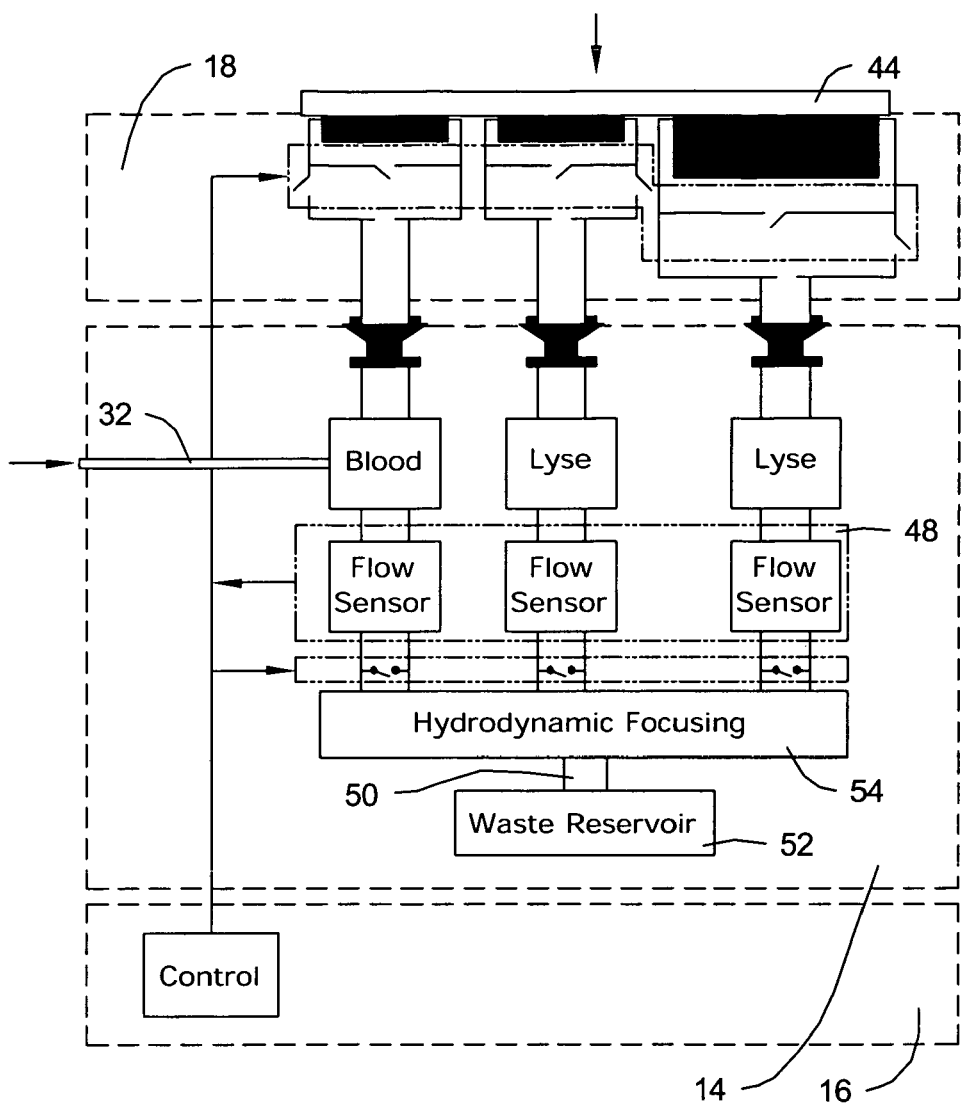
FIG. 4 is a more detailed schematic diagram showing the cytometer of FIG. 2 with the cover depressed.

FIG. 3 is a more detailed schematic diagram showing the cytometer of FIG. 2 with the cover 18 not yet depressed. FIG. 4 is a more detailed schematic diagram showing the cytometer of FIG. 2 with the cover depressed. The cover 18 is shown having a manual pressurizing element 44, pressure-chambers 46a, 46b and 46c, and control microvalves generally shown at 60. The light sources and detectors are not shown in these Figures.

There are three pressure chambers 46a, 46b and 46c, one for each fluid to be pressurized. In the illustrative example, pressure chamber 46a provides pressure to a blood sample reservoir 62, pressure chamber 46b provides pressure to a lyse reservoir 64, and pressure chamber 46c provides pressure to a sheath reservoir 66. The size and shape of each pressure chamber 46a, 46b and 46c may be tailored to provide the desired pressure characteristics to the corresponding fluid.

Pressure chamber 46a includes a first pressure chamber 70 and a second pressure chamber 72. A first valve 74 is provided between the first pressure chamber 70 and the second pressure chamber 72 for controllably releasing the pressure in the first pressure chamber 70 to a second pressure chamber 72. A second valve 76, in fluid communication with the second pressure chamber 72, controllably vents the pressure in the second pressure chamber 72. Each valve may include an array of electrostatically actuated microvalves that are individually addressable and controllable, as described in, for example, co-pending U.S. patent application Ser. No. 09/404,560, entitled "Addressable Valve Arrays for Proportional Pressure or Flow Control", and incorporated herein by reference. Pressure chambers 46b and 46c include similar valves to control the pressures applied to the lyse reservoir 64 and sheath reservoir 66, respectively. Alternatively, each valve may be an array of electrostatically actuated microvalves that are pulse modulated with a controllable duty cycle to achieve a controlled "effective" flow or leak rate.

The removable cartridge 14 has pressure receiving ports 34a, 34b, and 34c for receiving the controlled pressures from the cover 18. The controlled pressures are provided to the blood reservoir 62, lyse reservoir 64 and sheath reservoir 66, as shown. The lyse reservoir 64 and sheath reservoir 66 may be filled before the removable cartridge 14 is shipped for use, while the blood reservoir 62 is filled from sample collector port 32. A blood sample may be provided to the sample collector port 32, and through capillary action, the blood sample is sucked into the blood reservoir 62. Once the blood sample is in the blood reservoir 62, the cover 18 may be closed and the system may be pressurized.

A flow sensor is provided in-line with each fluid prior to hydrodynamic focusing. Each flow sensor 80, 100 and 102 measures the velocity of the corresponding fluid. The flow sensors may be thermal anemometer type flow sensors, such as microbridge type flow sensor. Microbridge flow sensors are described in, for example, U.S. Pat. Nos. 4,478,076, 4,478,077, 4,501,144, 4,651,564, 4,683,159, and 5,050,429, all of which are incorporated herein by reference. An output signal from each flow sensor 80, 100 and 102 is provided to controller or processor 40.

The controller or processor 40 opens the first valve 74 when the velocity of the blood sample drops below a first predetermined value and opens the second valve 76 when the velocity of the blood sample increases above a second predetermined value. Valves 84, 86, 94 and 96 operate in a similar manner to control the velocities of the lyse and sheath fluids.

During operation, and to pressurize the system, the manual pressurizing element 44 is depressed. In the example shown, the manual pressurizing element 44 includes three plungers, with each plunger received within a corresponding one of the first pressure chambers. The plungers create a relatively high non-precision pressure in the first pressure chambers. Lower, controlled pressures are built in the secondary chambers by opening the first valves 70, 84 and 94, which produce a controllable leak into the secondary chambers. If too much pressure builds up in the secondary pressure chambers, the corresponding vent valves 76, 86 and 96 are opened to relieve the pressure.

When closing the cover 18, the normally open first valves 74, 84 and 94 are closed while the vent valves 76, 86 and 96 are open. When a predetermined pressure P is achieved in the first pressure chambers, the vent valves 76, 86 and 96 are closed, and the first valves 74, 84 and 94 are opened to build a lower pressure P' in the secondary pressure chambers. The controlled pressure in the secondary pressure chambers provide the necessary pressures to the fluidic circuit of the removable cartridge 14 to produce fluid flow for the blood, lyse and sheath. The velocity of the fluid flow is then measured by the downstream flow sensors 80, 100 and 102. Each flow sensor provides an output signal that is used by the controller or processor 40 to control the operation of the corresponding first valve and vent valve to provide a desired and constant flow rate for each fluid.

Downstream valves generally shown at 110 may also be provided. Controller or processor 40 may close downstream valves 110 until the system is pressurized. This may help prevent the blood, lyse and sheath from flowing into the fluid circuit before the circuit is pressurized. In another illustrative example of the invention, downstream valves 110 are opened by mechanical action when the cover is closed.

Figure 5:
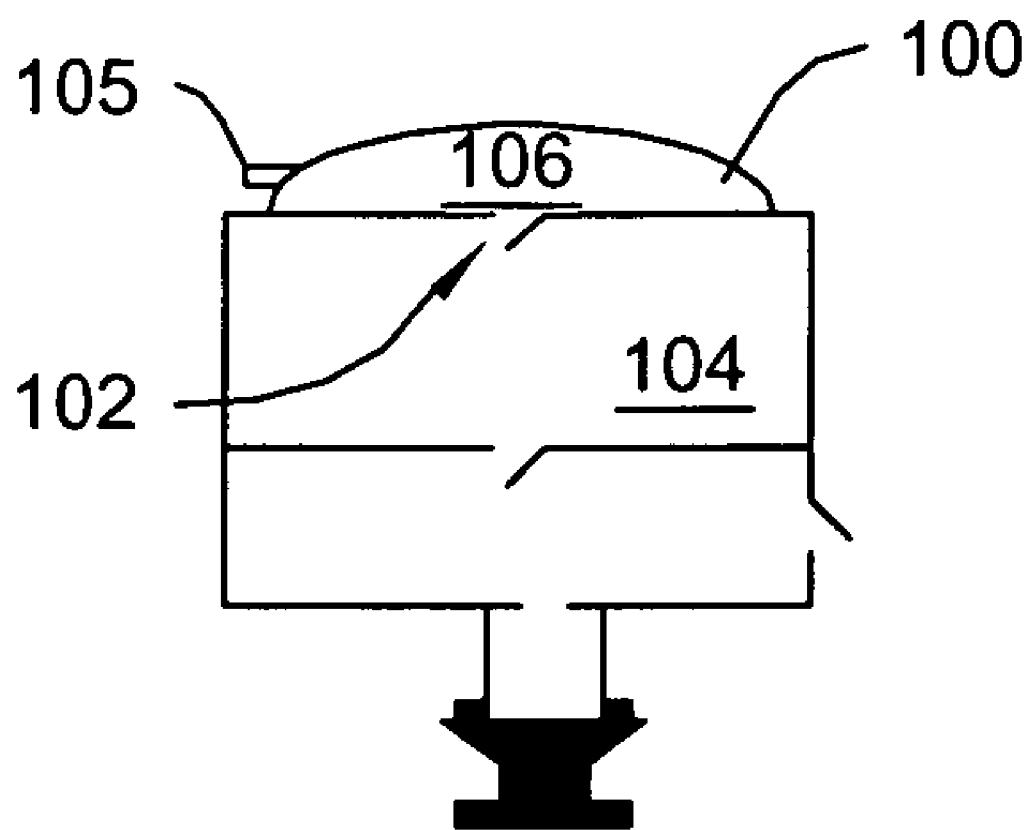
FIG. 5 is a schematic diagram showing an illustrative manual fluid driver having a bulb and check valve.

FIG. 5 is a schematic diagram showing an illustrative manual fluid driver having a bulb 100 and check valve 102. The check valve 102 may be a one way valve that allows air in but not out of the first pressure chamber 104. When the bulb 100 is depressed, the air in the interior 106 of the bulb 100 is forced through the check valve 102 and into the first pressure chamber 104. Another one-way vent valve 105 may be provided that allows air in from the atmosphere but not out of the interior 106 of the bulb 100. Thus, when the bulb is released, the one-way vent valve 105 may allow replacement air to flow into bulb 100.

Rather than using a manually operated fluid driver, it is contemplated that any relatively small pressure source may be used including, for example, an electrostatically actuated meso-pump. One such meso-pump is described in, for example, U.S. Pat. No. 5,836,750 to Cabuz, which is incorporated herein by reference.

Figure 6:
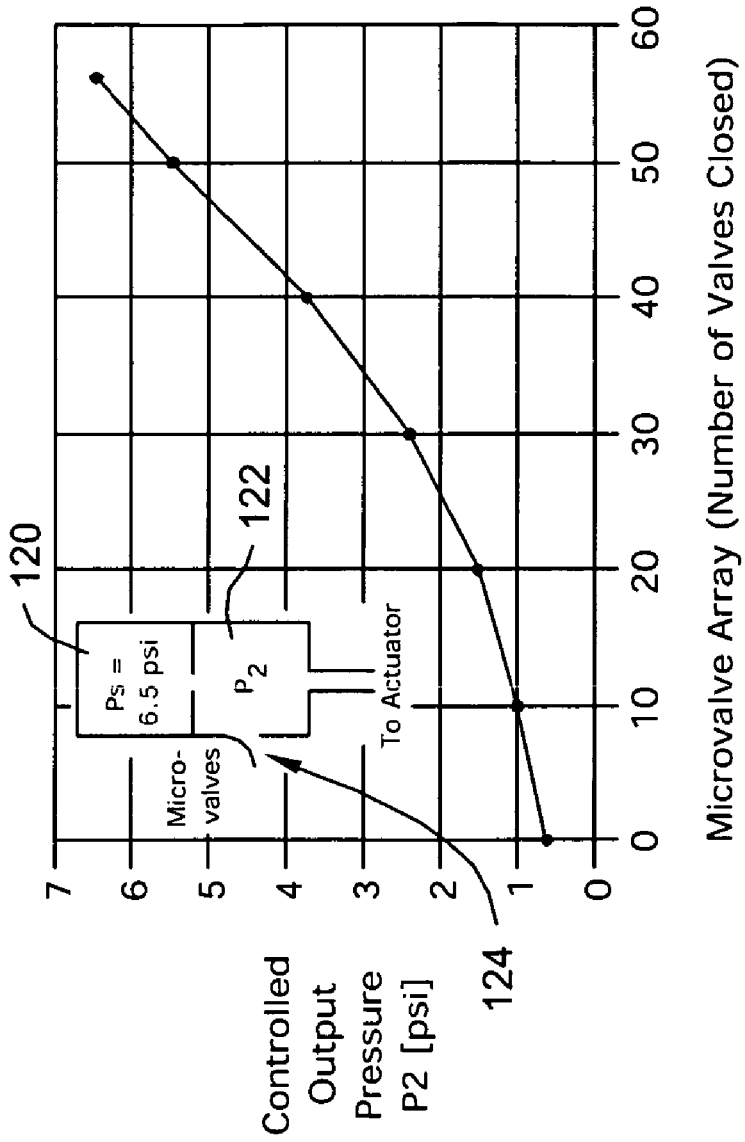
FIG. 6 is a graph showing proportional pressure control of an addressable array of microvalves.

FIG. 6 is a graph showing proportional pressure control produced by an 8×7 addressable array of microvalves. To create the graph shown in FIG. 6, 6.5 psi was applied to a first pressure chamber 120. A small opening was provided to a second pressure chamber 122. The microvalves are shown at 124, and vent the pressure in the second pressure chamber 122. By changing the number of addressable microvalves that are closed, the pressure in the second pressure chamber can be changed and controlled. In the graph shown, the pressure in the second pressure chamber 122 could be changed from about 0.6 psi, when zero of the 8×7 array of microvalves close, to about 6.5 psi, when all of the 8×7 array of microvalves are closed. These low power, micromachined silicon microvalves can be used for controlling pressures up to 10 psi and beyond.

Figure 7:
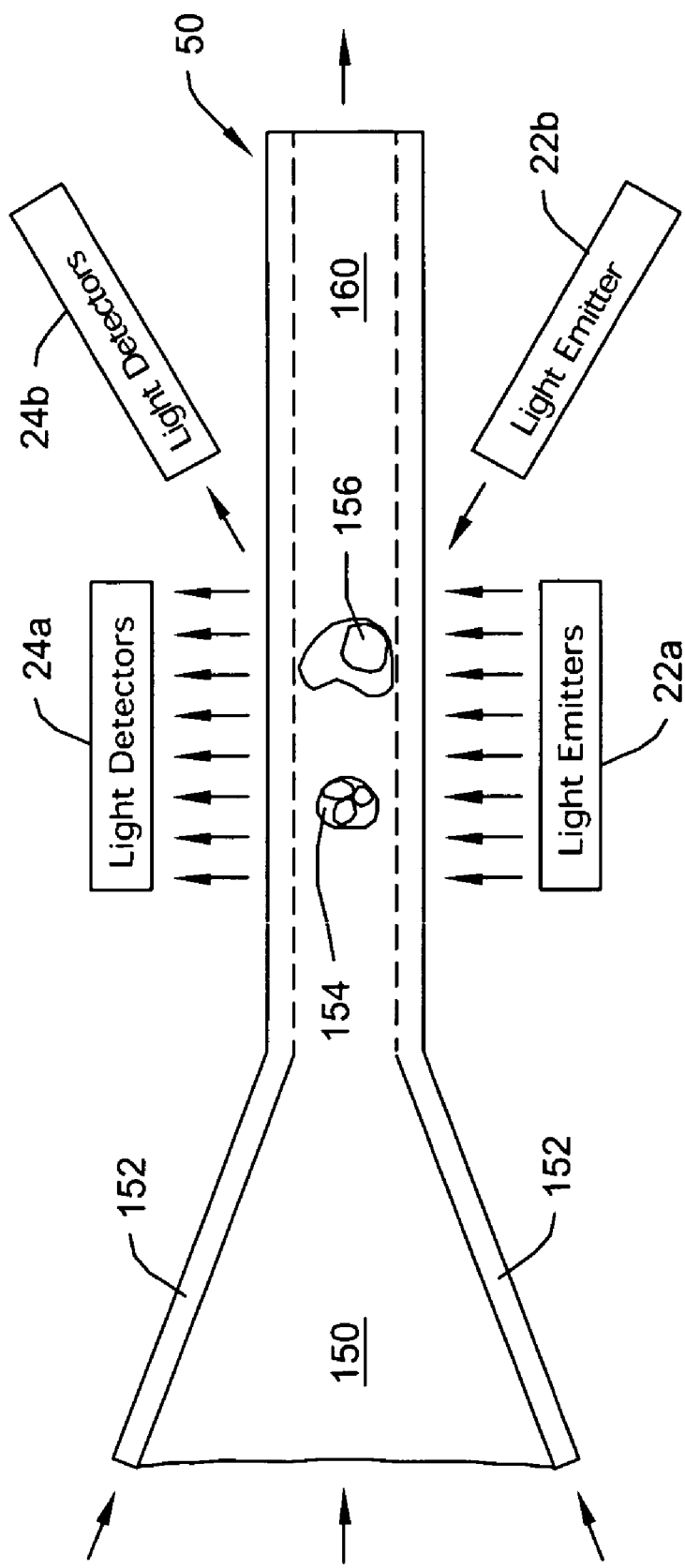
FIG. 7 is a schematic diagram showing the formation of a flow stream by the hydrodynamic focusing block 88 of FIG. 3.

FIG. 7 is a schematic diagram showing the formation of a flow stream and core by the hydrodynamic focusing block 88 of FIG. 3. The hydrodynamic focusing block 88 receives blood, lyse and sheath at controlled velocities from the fluid driver. The blood is mixed with the lyse, causing the red blood cells to be removed. The lysing solution may have a pH lower than that of the red blood cells. This is often referred to as red cell lysing or lyse-on-the-fly. The remaining white blood cells are provided down a central lumen 150, which is surrounded by sheath fluid to produce a flow stream 50. The flow stream 50 includes a core stream 160 surrounded by the sheath fluid 152. The dimensions of the channel are reduced as shown so that the white blood cells 154 and 156 are in single file. The velocity of the sheath fluid may be about 9 times or more than that of the core stream 160. However, the velocity of the sheath fluid and core stream 160 may remain sufficiently low to maintain laminar flow in the flow channel.

Light emitters 22a and 22b, and associated optics may be provided adjacent to one side of the flow stream 50. Light detectors 24a and 24b, and associated optics may be provided on another side of the flow stream 50 for receiving the light from the light emitters 22a and light from fluorescing particles via the flow stream 50. The output signals from the light detectors 24a and 24b are provided to controller or processor 40, wherein they are analyzed to identify and/or count selected white blood cells in the core stream 160.

Figure 8:
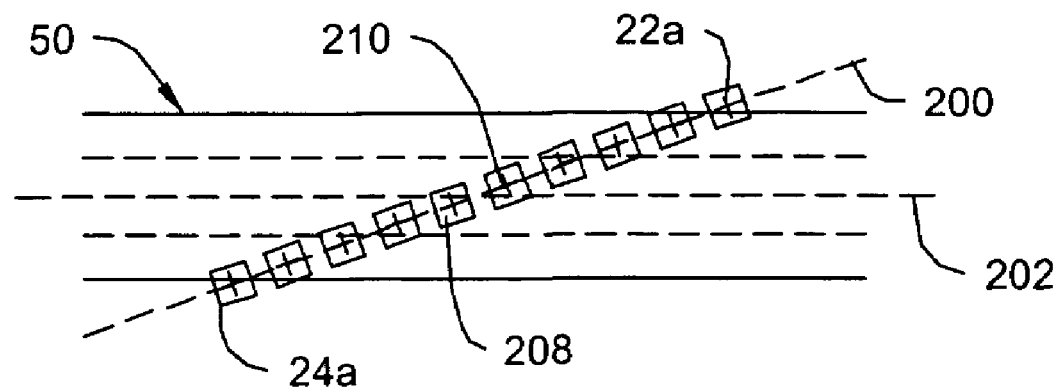
FIG. 8 is a schematic diagram showing an array of light sources and an array of light detectors for analysis of the core stream 160 of FIG. 7.

FIG. 8 is a schematic diagram showing an array 22a of light sources and an array 24b of light detectors for analysis of the core stream 160 via scattering of FIG. 7. The light sources are shown as "+" signs and the detectors are shown at boxes. In the example shown, the array of light sources is provided adjacent one side of the flow stream 50, and the array of light detectors is provided adjacent the opposite side of the flow stream. Each of the light detectors may be aligned with a corresponding one of the light sources. The array of light sources and the array of light detectors are shown arranged along a light source axis 200 that is slightly rotated relative to the axis 202 of the flow stream 50.

The array 22a of light sources may be an array of lasers such as vertical cavity surface emitting lasers (VCSELs) fabricated on a common substrate. Because of their vertical emission, VCSELs are ideally suited for packaging in compact instruments such as a miniaturized portable cytometer. Such cytometer may be wearable on a person's body. The VCSELs may be "red" VCSELs that operate at wavelengths that are less than the conventional 850 nm, such as in the 670 nm to 780 nm range. Red VCSELs may have a wavelength, power and polarization characteristic that is ideally suited for scatter measurements.

Some prior art cytometer bench models use a single 9 mW edge-emitting laser with a wavelength of 650 nm. The beam is focused to a 10×100 micron elongated shape to cover the uncertainty in particle position due to misalignment and width of the core stream. In contrast, the output power of the red VCSELs of the present invention, operating at 670 nm, is typically around 1 mW for a 10×10 micron emitter and 100-micron spacing. Thus, the total intensity of the light from a linear array of ten red VCSELs may be essentially the same as that of some prior art bench models.

Using a linear array of lasers oriented at an angle with respect to the flow axis 202 offers a number of important advantages over the single light source configuration of the prior art. For example, a linear array of lasers may be used to determining the lateral alignment of the path of the particles in the core steam. One source of uncertainty in the alignment of the particle stream is the width of the core flow, which leads to statistical fluctuations in the particle path position. These fluctuations can be determined from analysis of the detector data and can be used by the controller or processor 40 to adjust the valves of the fluid driver in order to change the relative pressures that are applied to the sample fluid and the supporting fluids to change the alignment of the selected particles in the flow stream.

To determine the lateral alignment of the cells in the fluid stream 50, the cells pass through several focused spots produced by the linear array of VCSELs. The cells produce a drop in signal in the corresponding in-line reference detectors. The relative strengths of the signals are used by the controller or processor 40 to determine the center of the particle path and a measure of the particle width.

Figure 9:
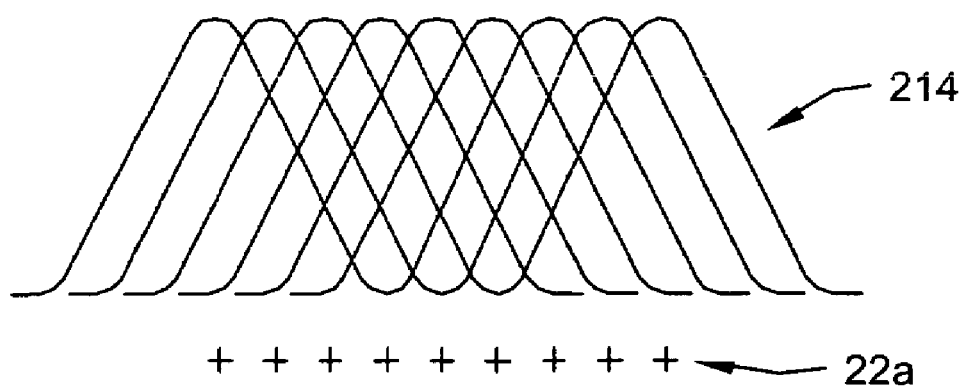
FIG. 9 is a graph showing the light intensity produced along the light source axis of FIG. 8.

For determining particle path and size, the lasers 22a may be focused to a series of Gaussian spots 214 (intensity on the order of 1000 W/cm$^2$) in the plane of the core flow. The spots 214 may be about the same size as a white blood cell (10-12 um). Illustrative Gaussian spots 214 are shown in FIG. 9. Arrays 24a of detectors and their focusing optics are provided on the opposite side of the fluid stream 50. Lenses with fairly large F-numbers are used to provide a working space of several hundred microns for the cytometer section of the removable cartridge.

Another advantage of using a linear array 22a of lasers rather than a single laser configuration is that the velocity of each cell may be determined. Particle velocity can be an important parameter in estimating the particle size from light scatter signals. In conventional cytometry, the particle velocity is extrapolated from the pump flow rates. A limitation of this approach is that the pumps must be very precise, the tolerance of the cytometer flow chambers must be tightly controlled, no fluid failures such as leaks can occur, and no obstructions such as microbubbles can be introduced to disturb the flow or core formation.

To determine the velocity of each cell, the system may measure the time required for each cell to pass between two adjacent or successive spots. For example, and with reference to FIG. 8, a cell may pass detector 208 and then detector 210. By measuring the time required for the cell to travel from detector 208 to detector 210, and by knowing the distance from detector 208 to detector 210, the controller or processor 40 can calculate the velocity of the cell. This would be an approximate velocity measurement. This is often referred to as a time-of-flight measurement. Once the velocity is known, the time of travel through the spot on which the particle is centered (a few microseconds) may provide a measure of particle length and size.

It is contemplated that the particle velocity can also be used to help control the fluid driver. To reduce the size, cost and complexity of the present invention, the replaceable cartridge of FIG. 1 may be manufactured from a plastic laminate or molded parts. While such manufacturing techniques may provide inexpensive parts, they are typically less dimensionally precise and repeatable, with asymmetrical dimensions and wider tolerance cross-sections. These wider tolerances may produce variations in particle velocity, particularly from cartridge to cartridge. To help compensate for these wider tolerances, the time-of-flight measurement discussed above can be used by the controller or processor 40 to adjust the controlled pressures applied to the blood, lyse and sheath fluid streams such that the particles in the core stream have a relatively constant velocity.

To further evaluate the cell size, it is contemplated that laser beams may be focused both along the cell path and across the cell path. Additionally, multiple samples across the cell may be analyzed for texture features, to correlate morphological features to other cell types. This may provide multiple parameters about cell size that may help separate cell types from one another.

Another advantage of using a linear array 22a of lasers rather than a single layer configuration is that a relatively constant light illumination may be provided across the flow channel. This is accomplished by overlapping the Gaussian beams 214 from adjacent VCSELs 22a, as shown in FIG. 9. In prior art single laser systems, the light illumination across the flow channel typically varies across the channel. Thus, if a particle is not in the center of the flow channel, the accuracy of subsequent measurements may be diminished.

Figure 10:
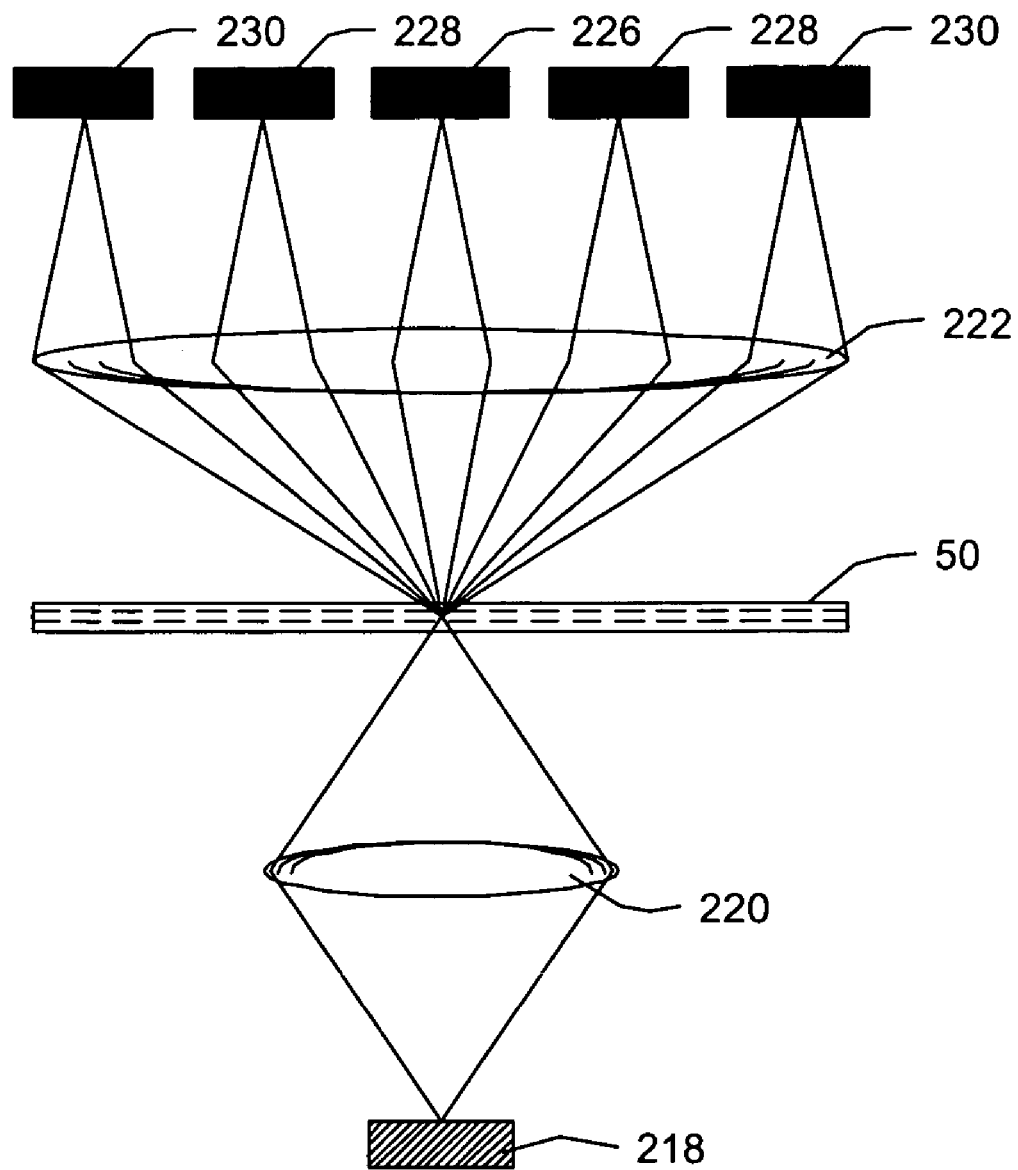
FIG. 10 is a schematic diagram showing an illustrative light source and detector pair of FIG. 8.

To perform the above described measurements, each detector 24a in FIG. 8 may be a single in-line detector. To measure FALS and SALS scatter, however, each detector 24a may further include two annular detectors disposed around the in-line detector, as shown in FIG. 10. Referring to FIG. 10, a VCSEL 218 is shown providing light in an upward direction. The light is provided through a lens 220, which focuses the light to a Gaussian spot in the plane of the core flow. Lens 220 may be a microlens or the like, which is either separate from or integrated with the VCSEL 218. The light passes through the core flow, and is received by another lens 222, such as a diffractive optical element. Lens 222 provides the light to in-line detector 226 and annular detectors 228 and 230. The in-line detector 226 detects the light that is not significantly scattered by the particles in the core stream. Annular detector 228 detects the forward scatter (FALS) light, and annular detector 230 detects the small angle scatter (SALS) light.

Figure 11:
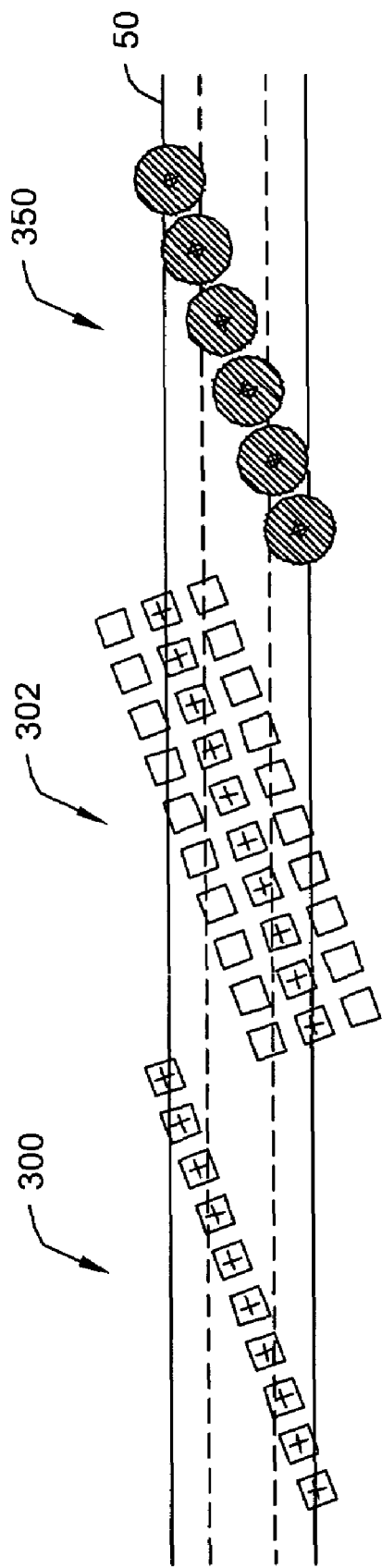
FIG. 11 is a schematic diagram showing three separate arrays of light sources and detectors, each positioned along a different light source axis that is slightly rotated relative to the central flow axis of the flow stream of FIG. 7.

Figure 11 shows another illustrative example of the present invention that includes three separate arrays of light sources and light detectors. Each array of light sources and light detectors are positioned along a different light source axis that is slightly rotated relative to the central flow axis of the flow stream. By using three arrays, the optics associated with each array may be optimized for a particular application or function. For detecting small angle scattering (SALS), laser light that is well-focused on the plane of the core flow is desirable. For detecting forward scattering (FALS), collimated light is desirable.

Referring specifically to FIG. 11, a first array of light sources and light detectors is shown at 300. The light sources and light detectors are arranged in a linear array along a first light source axis. The first light source axis is rotated relative to the flow axis of the flow stream. The light sources and light detectors may be similar to that described above with respect to FIG. 8, and may be used to measure, for example, the lateral alignment of the cells in the flow stream, the particle size, and the velocity of the particles.

Figure 12:
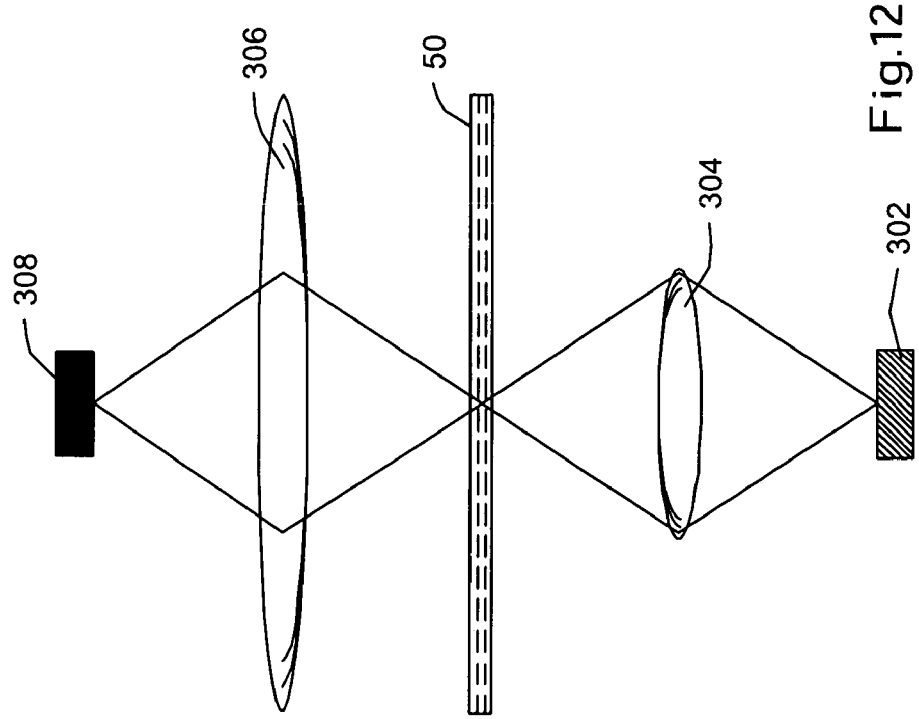
FIG. 12 is a schematic diagram showing an illustrative light source and detector pair of the first array shown in FIG. 11.

FIG. 12 is a schematic diagram showing an illustrative light source and detector pair of the first array 300 shown in FIG. 11. A VCSEL 302 is shown providing light in an upward direction. The light is provided through a lens 304, which focuses the light to a Gaussian spot in the plane of the core flow. The light passes through the core flow, and is received by another lens 306. Lens 306 provides the light to in-line detector 308. The in-line detector 308 detects the light that is not significantly scattered by the particles in the core stream.

A second array of light sources and light detectors is shown at 310. The light sources are arranged in a linear array along a second light source axis that is rotated relative to the flow axis of the flow stream. The light detectors include three linear arrays of light detectors. One array of light detectors is positioned in line with the linear array of light sources. The other two linear arrays of light detectors are placed on either side of the in-line array of light detectors, and are used for measuring the small angle scattering (SALS) produced by selected particles in the flow stream.

Figure 13:
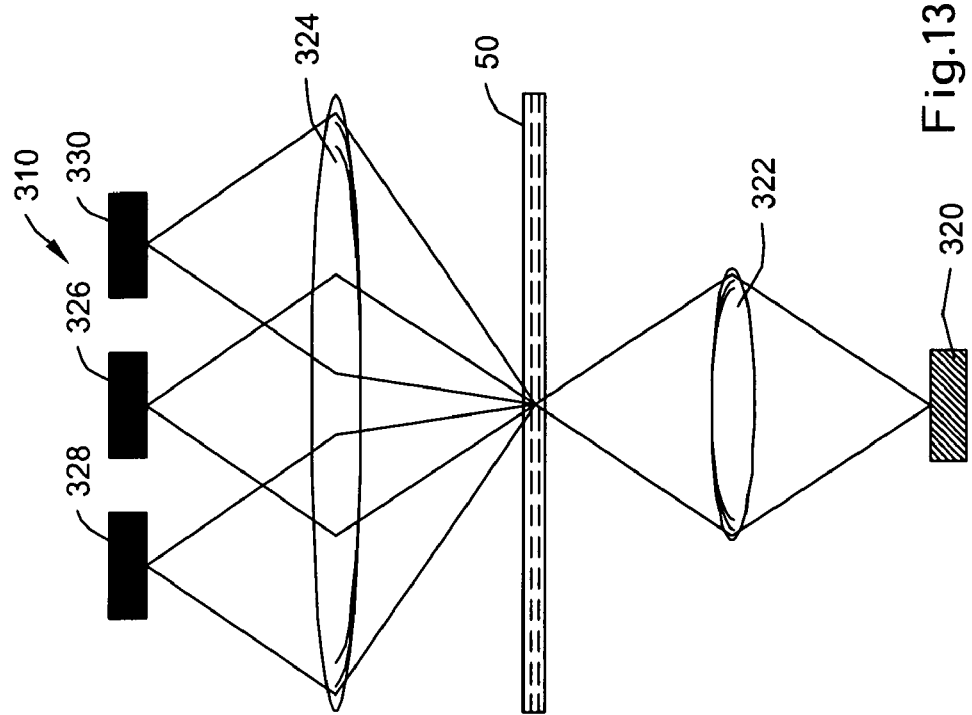
FIG. 13 is a schematic diagram showing an illustrative light source and detector pair of the second array shown in FIG. 11.

FIG. 13 is a schematic diagram showing an illustrative light source and corresponding detectors of the second array shown in FIG. 11. A VCSEL 320 is shown providing light in an upward direction. The light is provided through a lens 322, which focuses the light to a Gaussian spot in the plane of the core flow. The light passes through the core flow, and is received by another lens 324, such as a diffractive optical element (DOE) 324. Lens 324 provides the light to the in-line detector 326 and the two corresponding light detectors 328 and 330 placed on either side of the in-line light detector 326.

The in-line detector 326 may be used to detect the light that is not significantly scattered by the particles in the core stream. Thus, the in-line linear array of light detectors of the second array 302 may be used to provide the same measurements as the in-line array of detectors of the first array 300. The measurements of both in-line arrays of detectors may be compared or combined to provide a more accurate result. Alternatively, or in addition, the in-line detectors of the second array 302 may be used as a redundant set of detectors to improve the reliability of the cytometer.

It is contemplated that the in-line detectors of the second array 302 may also be used in conjunction with the in-line detectors of the first array 300 to more accurately determine the time-of-flight or velocity of the particles in the flow stream. The measurement may be more accurate because the distance between detectors may be greater. As indicated above, by knowing the velocity of the particles, small variations in the flow rate caused by the fluid driver can be minimized or removed by the controller.

Light detectors 328 and 330 of FIG. 13 are used to measure the small angle scattering (SALS) produced by selected particles in the flow stream. The light detectors 328 and 330 may therefore be spaced sufficiently from the in-line detector 326 to intercept the small angle scattering (SALS) produced by selected particles in the flow stream.

Referring back to FIG. 11, a third array of light sources and light detectors 350 may be provided to measure the forward angle scattering (FALS) produced by selected particles in the flow stream. The light sources are arranged in a linear array along a third light source axis that is rotated relative to the flow axis of the flow stream. Each light source may have a corresponding light detector, and each light detector is may have an annular shape with a non-sensitive region or a separate in-line detector in the middle. The annular shaped light detectors may be sized to intercept and detect the forward angle scattering (FALS) produced by selected particles in the flow stream.

Figure 14:
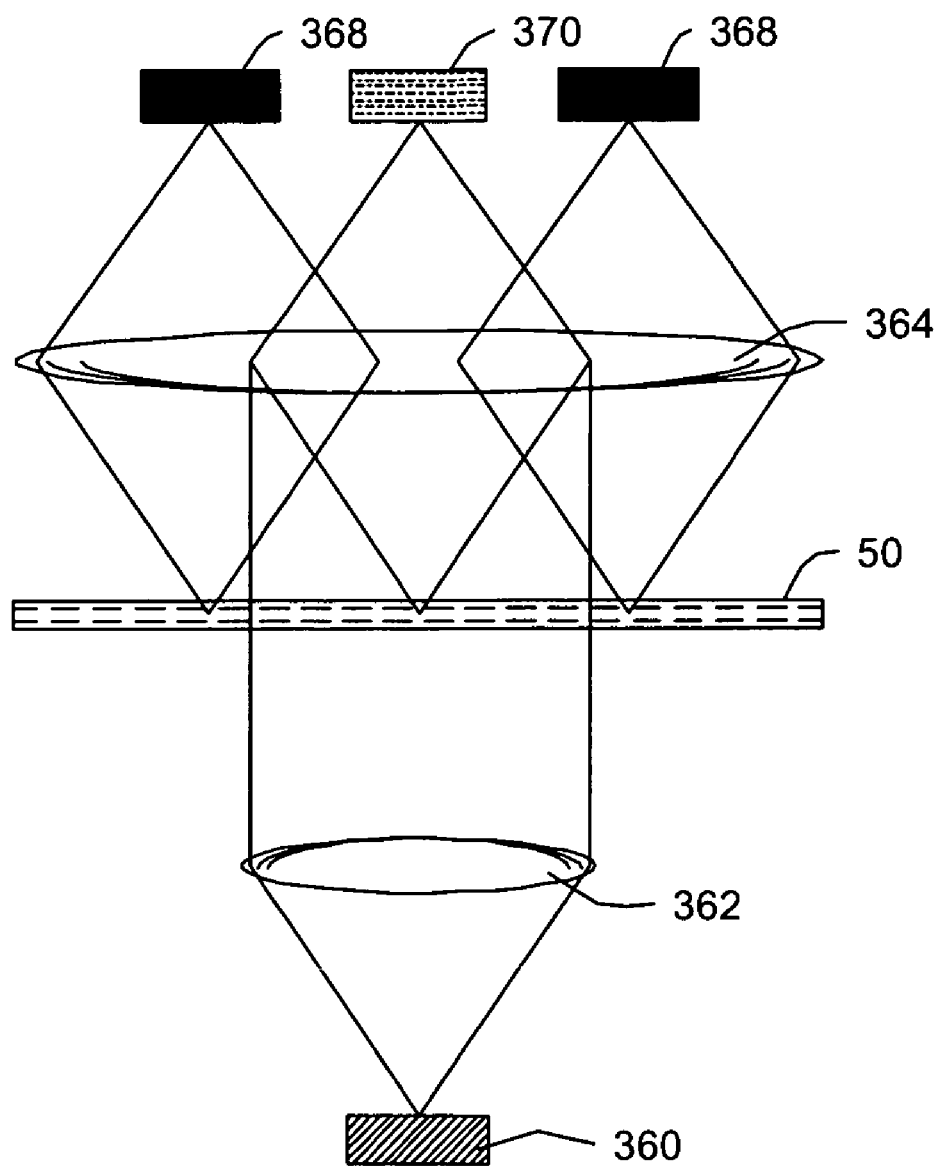
FIG. 14 is a schematic diagram showing an illustrative light source and detector pair of the third array shown in FIG. 11.

FIG. 14 is a schematic diagram showing an illustrative light source and detector pair of the third array of light sources and light detectors 350 shown in FIG. 11. A VCSEL 360 is shown providing light in an upward direction. The light is provided through a lens 362 such as a collimating lens, which provides substantially collimated light to the core flow. As indicated above, collimated light is desirable for detecting forward scattering (FALS) light. The light passes through the core flow, and is received by another lens 364. Lens 364 provides the received light to the annular shaped detector 368.

The annular shaped detector 368 may be sized to intercept and detect the forward angle scattering (FALS) produced by selected particles in the flow stream. A non-sensitive region or a separate in-line detector 370 may be provided in the middle of the annular shaped detector 368. If a separate in-line detector 370 is provided, it can be used to provide the same measurement as the in-line detectors of the first array 300 and/or second array 302. When so provided, the measurements from all three in-line arrays of detectors of first array 300, second array 302 and third array 350 may be compared or combined to provide an even more accurate result. The in-line detectors of the third array 302 may also be used as another level or redundancy to improve the reliability of the cytometer.

It is contemplated that the in-line detectors of the third array 350 may also be used in conjunction with the in-line detectors if the first array 300 and/or second array 302 to more accurately determine the time-of-flight or velocity of the particles in the flow stream. The measurement may be more accurate because the distance between detectors may be greater. As indicated above, by knowing the velocity of the particles, small variations in the flow rate caused by the fluid driver can be minimized or removed by the controller.

By using three separate arrays of light sources and detectors, the optics associated with each array can be optimized for the desired application. As can be seen, the optics associated with the first array 300 are designed to provide well-focused laser light on the plane of the core flow. This helps provide resolution to the alignment, size and particle velocity measurements performed by the first array 300. Likewise, the optics associated with the second array 302 are designed to provide well-focused laser light on the plane of the core flow. Well focused light is desirable when measuring the small angle scattering (SALS) produced by selected particles in the flow stream. Finally, the optics associated with the third array 350 are designed to provide collimated light to the core flow. As indicated above, collimated light is desirable when measuring forward angle scattering (FALS) produced by selected particles in the flow stream.

Figure 15:
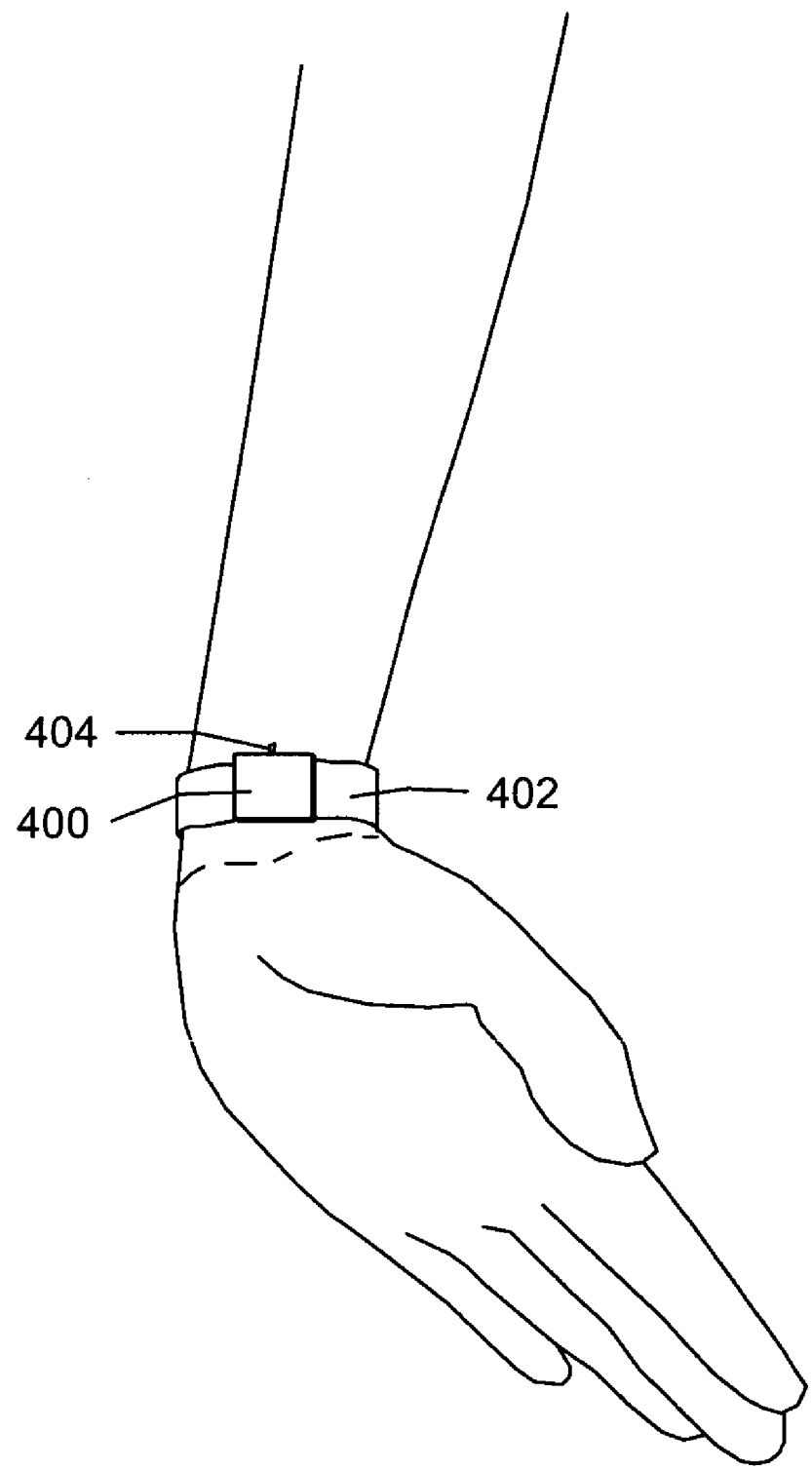
FIG. 15 is a perspective view of an illustrative example of the miniaturized portable cytometer adapted to be worn around the wrist.

FIG. 15 is a perspective view of an illustrative example of the miniaturized portable cytometer of the present invention adapted to be worn around the wrist. This cytometer 400 may be similar to that shown in FIG. 1. A band 402 secures cytometer 400 to the wrist of a user.

As indicated above, the user may obtain a removable cartridge and provide a blood sample to the sample collector port 32 (see FIG. 1) of the removable cartridge. The blood sample may be collected by, for example, a finger prick. The user may then insert the removable cartridge into the housing, and manually pressurize the system. The miniaturized portable cytometer may then provide a reading that indicates if the user should seek medical treatment. The reading may be a visual reading, an audible sound or any other suitable indicator.

Rather than obtaining the blood sample by a finger prick or the like, it is contemplated that a catheter 404 or the like may be inserted into a vein of the user and attached to the sample collector port 32. This may allow the system to automatically collect a blood sample from the user whenever a reading is desired. Alternatively, it is contemplated that the miniaturized portable cytometer may be implanted in the user, with the sample collector port 32 connected to a suitable blood supply.

Figures 16, 17:
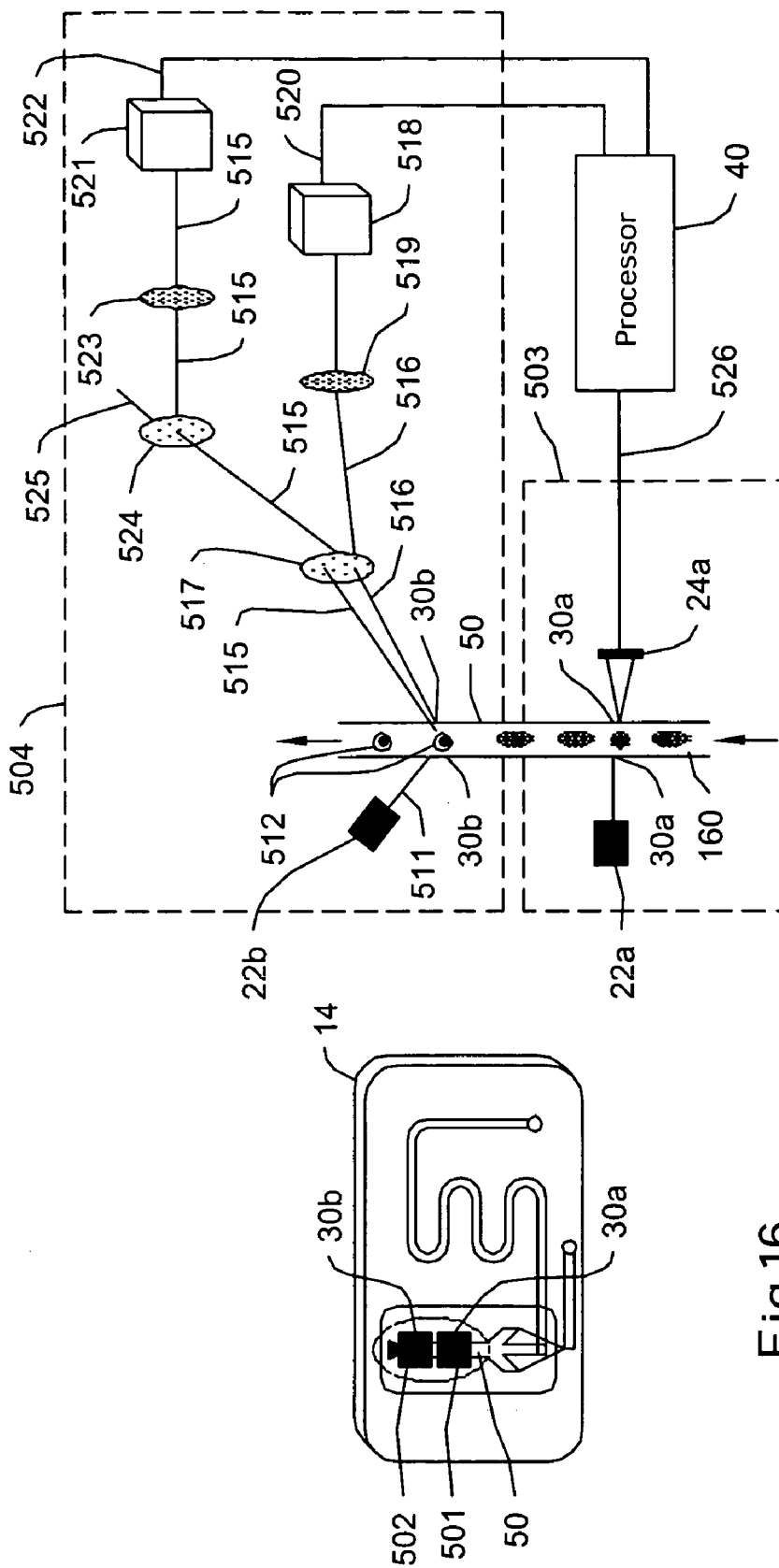
FIG. 16 is an illustration of a miniaturized portable cytometer cartridge incorporating the scattering and fluorescence optical subsystems.
FIG. 17 shows the layout of the scattering and fluorescence detection systems.

FIG. 16 shows a cytometer cartridge 500 showing a scattering optical subsystem 501 and fluorescent optical subsystem 502. Optical subsystem 501 includes windows or openings 30a on each side of flow channel 530 and optical subsystem 502 includes windows or openings 30b. In each subsystem, there is a window or opening on each side of flow channel 530. The openings may have optical inserts or lenses. This cytometer may be implemented for wearing, attachment on, or insertion in a person's body.

FIG. 17 shows systems 503 and 504 which incorporate optical subsystems 501 and 502, respectively. System 503 also includes VCSEL array 22a and detector array 24a for scattering measurements of particles, such as white blood cells, in core stream 160. This system is may be used for the counting and classification of lymphocytes and neutrophils. Self-alignment is may be enabled by a red VCSEL-array based optical subsystem. Illustrative examples of scattering system 503 are described above.

System 504 is a fluorescent exciting and detection mechanism which may be used for identifying and counting specific subclasses of white blood cells and blood-based proteins. The detection of subclasses of white blood cells is enabled by the availability of suitable antibodies, many of which are commercially available in a fluorescently conjugated form. FIG. 18 shows an outline sketch of blood composition and the cells that may be subject to counting and identification by fluorescent system 504. The red blood cells are removed from the sample to be looked with the cytometer by lysing as noted above. The platelets are kept as the small size does not affect the results of the cytometer when checking the white blood cells. For an illustrative example, the CD4-positive T-cells 505, shown in the structure of FIG. 18 have proportions and counts in blood that may be very important in following a clinical course of an HIV infection. An antibody with a marker added that associates with CD4 may be mixed in the sample of blood to get a resultant "Y"-looking structure of the antibody (AB) 506 and its marker (M) 507, attached to CD4 cell 505, as shown in FIG. 19a. Light source 22b may emit light which may be absorbed by marker 507. In response, marker 507 fluoresces and emits light of a particular wavelength which may be detected to identify CD4 cell 505.

Checking blood for anthrax may be another application of the present cytometer. Antibodies 508 for the anthrax-causing bacteria 509 may be mixed with the blood sample. The antibodies may associate with bacteria 509. The antibodies may have markers 510 that fluoresce upon impingement of light. The "Y" structure of antibody 508 is shown in FIG. 19b. Markers 510 emit a light of a particular bandwidth which may be different from the bandwidth of marker 507 of antibody 506 for CD4 cell 505. So the anthrax problem may be identified separately from the HIV problem in the same blood sample test by the fluorescent emissions having different wavelengths, colors or signatures. The number of different problems being detected at the same time in the same blood sample may be many more than two.

For another illustrative example, Neupogen$^R$ (a type of protein) has been regarded as used to provide neutrophil counts in cancer patients undergoing myelosuppressive chemotherapy. While doing this therapy, there may a need to accurately monitor the white blood cell counts (specifically neutrophils, monocytes and platelet counts during the Neupogen$^R$ therapy period). The present cytometer may be used by untrained personnel to monitor such chemotherapy patients in their homes.

The present miniaturized portable cytometer may be use in biowarfare. It may be used for quantitative detection and identification of biowarfare agents. This detection and identification may be based antibody-antigen type immunoassay that may be implemented with fluorescent measurements. The environment, water and food may be monitored for any possible presence of biological agents. It would involve sample collection and preparation appropriated for the present cytometer. Other applications of the cytometer may include high throughput analysis (using the fluorescent detection features) and sequencing of DNA and RNA, studying the response of cell to potential drugs, immnunophenotyping of leukemia and lymphomas and monitoring residual disease in cancer patients, and cell sorting and cell isolation, including high-speed separation of rare event populations. Note that the above-mentioned applications, and other applications and uses may be accomplished with the single, portable, miniaturized, integrated scattering and multi-color fluorescent, low-power, low-cost cytometry instrument having a compact precision fluid driving system, not requiring operator intervention or adjustment during the analytical phase, not requiring trained personnel to operate the instrument, and using sanitary, disposable plastic- or other material-based microfluidic cartridges 14 having integrated optics and internal blood sample processing, among other features.

System 504 of FIG. 17 has a laser light source 22b positioned to direct Light 511 at particles 512 flowing single file through flow channel 530. For Illustrative purposes, particles 512 may include structures 513 and 514 of FIGS. 19a and 19b, respectively. Light 511 may be from a red or a blue laser source, such as a light emitting diode (LED), which may have a bandwidth of, for example, 650 to 700 nanometers or 380 to 420 nanometers, respectively. Other types of sources having appropriate wavelengths may be used for light 511. As light 511 impinges fluorescent markers 507 and 510, these markers fluoresce and emit light 515 and 516, respectively. Since the markers are different from each other, light 515 and light 516 have different wavelengths. Thus, structures 513 and 514 not only may be identifiable by the wavelengths of their emitted light but can be differentiated from each other in the same sample, blood or otherwise. Light 515 and 516 may go to a dichroic beam splitter 517 which separates the two beams by directing each of them in different directions. Beam 516 may go to a fluorescence photo detector 518 for detection and conversion of light 516 into an electrical signal 520 to processor 40. Beam 515 may go to a fluorescence photo detector 521 for detection and conversion of light 515 into an electrical signal 522 to processor 40. Band pass filter 519, which is in the path of beam 516, may filter out light 511 from light source 22b that managed to be present in beam 516. Band pass filter 523 may serve the same purpose for beam 515 as filter 519 for beam 515. A mirror 524 may be used to redirect beam 515 for purposes of detector 521 location for the possibility of more compact packaging of detection system 504 or for other reasons. Mirror 524 may on the other hand be another dichroic beam splitter for splitting out light 525 of a wavelength different from that of beams 515 and 516. More splitters might be used in a cascade-like or other structure to split out light of still other frequencies. Also going to processor 40 is a signal from detector array 24a of scattering detection system 503.

Splitter 517 may be replaced with other mechanisms for separating out the light of various wavelengths or selecting certain wavelengths. They may include notch and step function filters of various kinds, tunable diffraction gratings, thin film dielectric stacks, mirror beam splitters, photonic bandgap filters, photonic crystals, tunable band pass filters, etalon comb and other structures, wafers having light guides with structural or other filtering, silicon or glass wafers having a waveguide and perforations of a specific size and pitch for absorbing/filtering, and so on.

Figure 20:
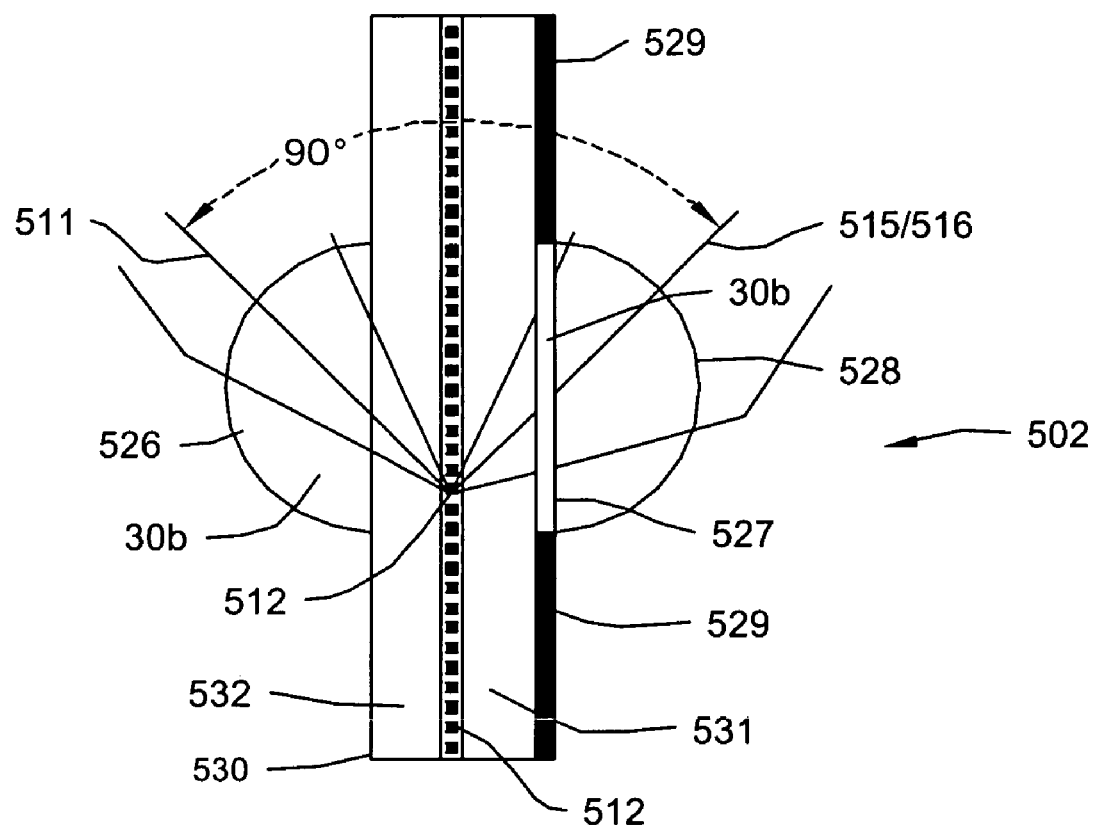
FIG. 20 shows the interaction of the light and optics for the fluorescence system.

FIG. 20 shows the structure of the fluorescence optical subsystem 502. A beam 511 may be emitted by light source 22b and focused onto a particle 512 by a microlens 526 through window 30b. Light beam 511 may or may not be collimated. Particle 512 may have a marker that fluoresces and emits a light beam 515, 516 through window 30b, a thin film coating filter 527 and a microlens 528, respectively. Filter 527 may filter out light 511 from light source 22b. Filter 527 may be a dielectric stack situated under lens 528 and be a notch or step function filter to block source 22b light 511. Lens 528 may focus fluorescent light emitted from the marker into a beam 515/516 which may go on to a beam splitter such as splitter 517. Beam 515/516 may or may not be collimated. An opaque or absorptive layer 529 is formed around or before and after window 30b or lens 528 on a glass, quartz or plastic (laminated or not) substrate 531 of flow channel 530. Layer 529 may block any light 511 emanating from light source 22b from exiting out with fluorescent light 515/516. Layer or blocking filter 529 may a thin film that is black or opaque to the wavebands desired to be blocked. Filter 529 could be a notch or step function filter. The other glass, quartz or plastic (laminated or not) substrate 532 forms flow channel 530 for the core flow of particles 512. The material of substrates 531 and 532, windows 30b and lens 526 and 528 should not contain ingredients that may fluoresce. In one illustrative example, the direction of light 511 from source 22b may be about 90 degrees relative to the direction of fluorescent light 515/516 emitted from particle 512. This angle between source light 511 and emitted fluorescent light 515/516 may effectively reduce or eliminate source light emanating out with fluorescent light 515/516. The angle of the direction of light 511 from source 22b in the example may be about 45 degrees relative to the direction of the longitudinal dimension flow channel 530 or the direction of the core flow of particles 512. However, in some applications, the angle between the directions of light 511 and light 515/516 may be between 0 and 120 degrees.

Figure 21A:
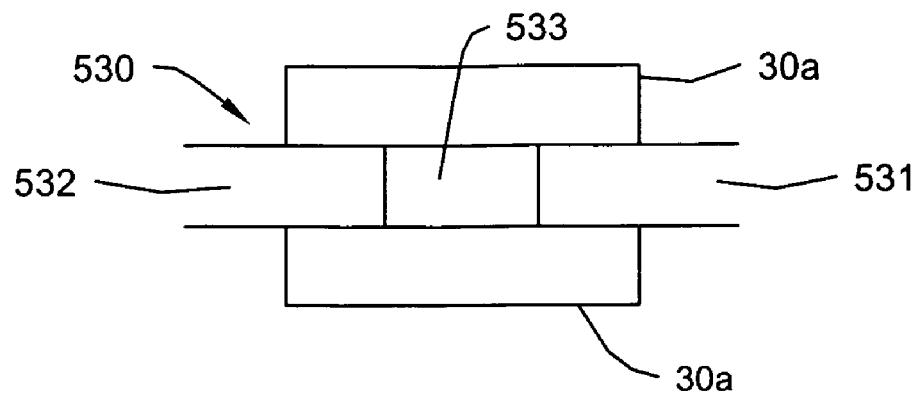
FIGS. 21a, 21b, 21c, 21d and 21e show the optical structure relative to the flow channel for the scattering and fluorescence systems, respectively.
Figure 21B:
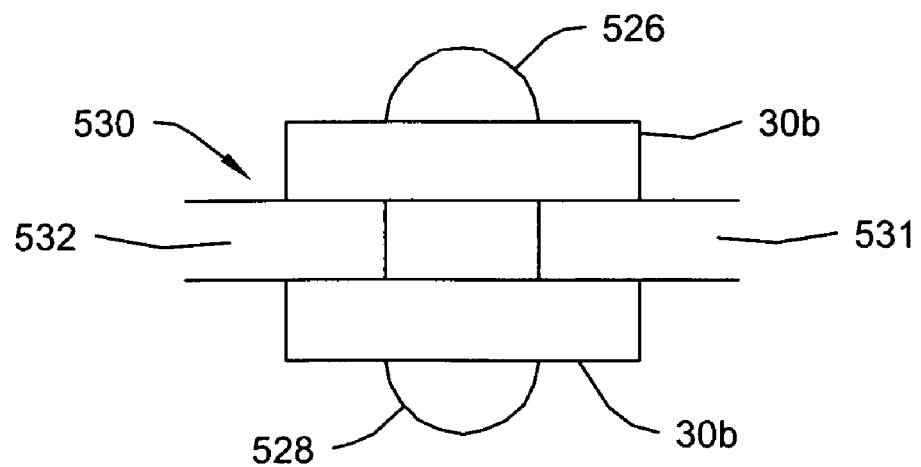

FIG. 21a shows an end view of flow channel 530 for scattering optical subsystem 501 and FIG. 21b shows an end view of flow channel 530 for fluorescence optical subsystem 502. The thicknesses of substrates 531 and 532 are about 100 to 200 microns. The thicknesses of windows 30a and 30b are about 25 to 30 microns. Microlenses 526 and 528 may be diffractive or refractive, plastic or glass and be aspheric lenses about 500 microns in diameter. Channel 533 may be laser cut.

Figure 21C:
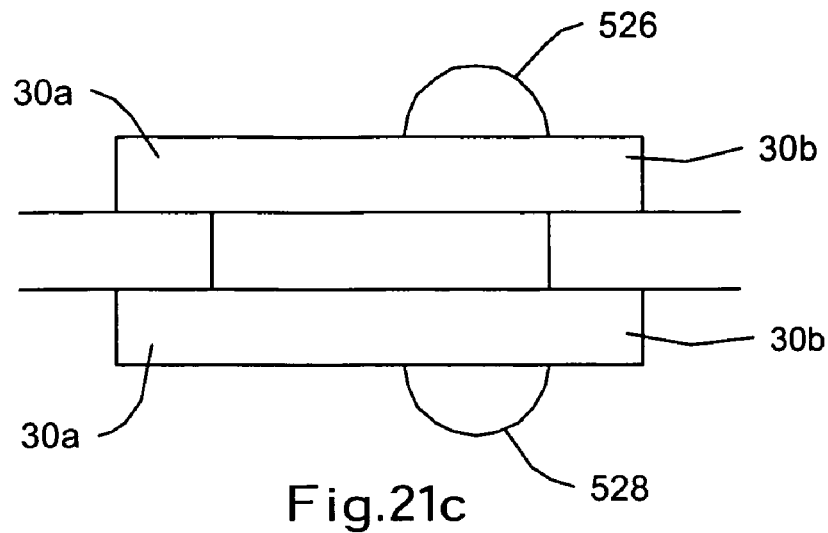
Figure 21D:
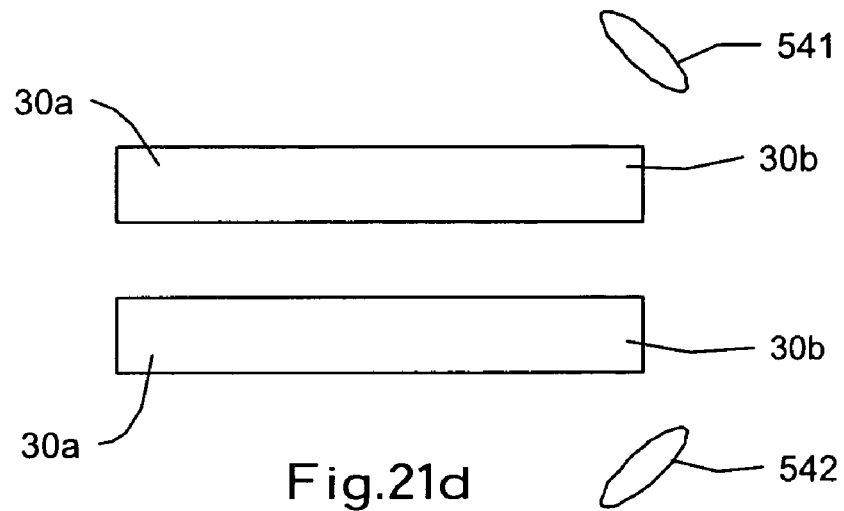
Figure 21E:
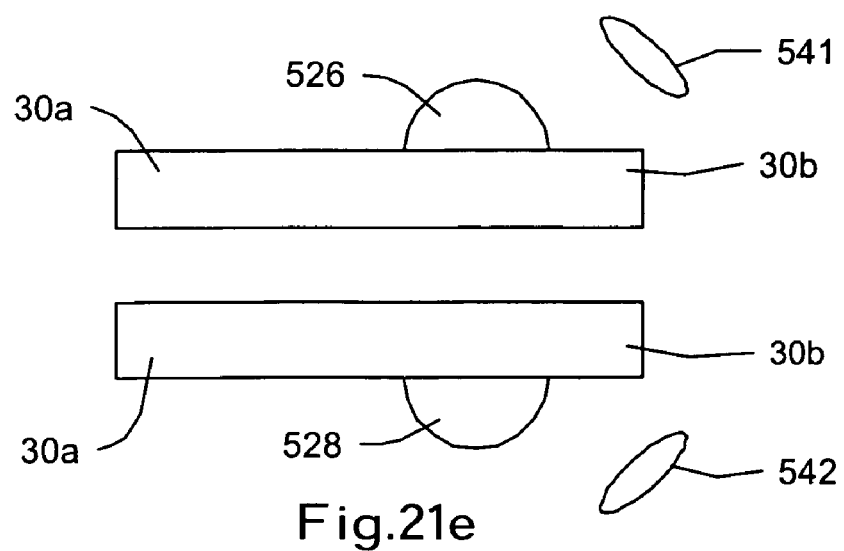
Figure 22:
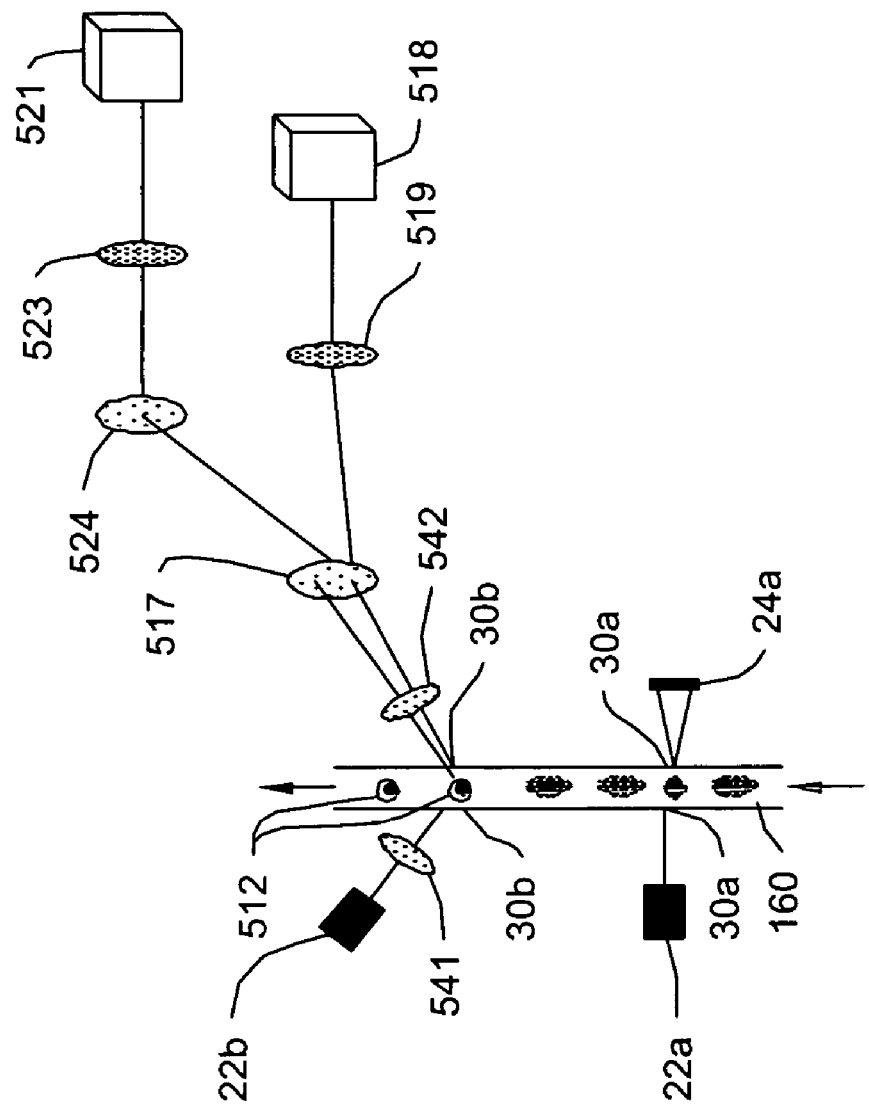
FIG. 22 shows a layout of the scattering and fluorescence detection systems having discrete lenses apart of the flow channel.

FIGS. 21c, 21d and 21e are variations of FIGS. 21a and 21b. FIG. 21c shows a flow channel having windows or openings 30a and 30b. Openings or windows 30a and 30b may be one window on each side of the flow channel, respectively. The openings may have optical inserts or lenses in them. Micro lenses 526 and 528 or other types of lenses may be formed on, attached to, inserted in, situated on or formed as an integral portion of openings or windows 30b and 30a which may be one piece on each side of the channel. FIG. 21d illustrates windows 30a and 30b without micro lenses attached or formed on them, but with lenses 541 and 542 situated at a certain and appropriate distance from them. FIG. 21e shows a window configuration with both micro lenses 526 and 528 along with detached lenses 541 and 542, respectively. FIG. 22 shows a diagram of cytometer configuration of FIG. 17, but with the placement of lenses 541 and 542. As noted above, windows and openings 30b may or may not have micro lenses in addition to lenses 541 and 542.

Figure 23:
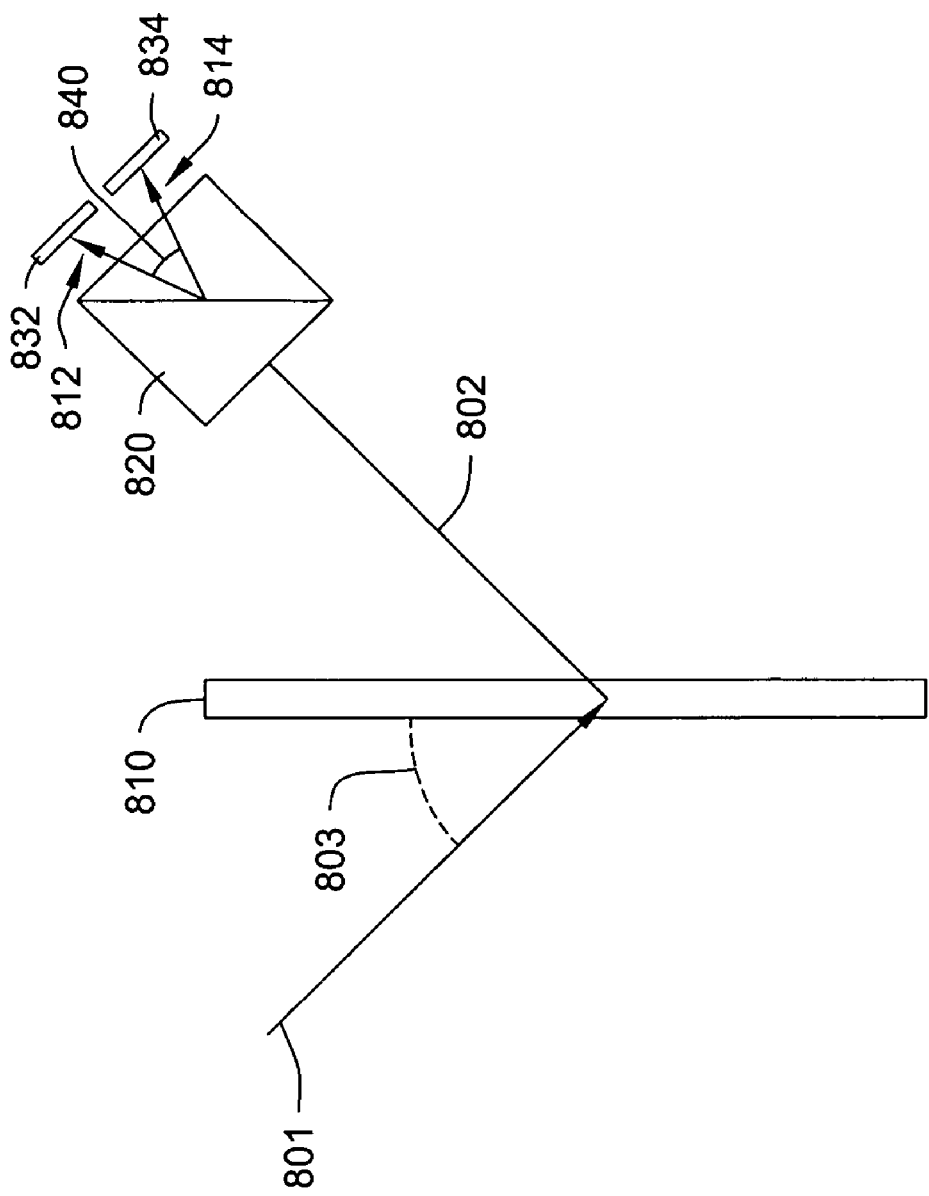
FIG. 23 is a schematic diagram showing an illustrative optical detection system that includes a polarizing beamsplitter, which may help provide further information regarding particles and/or particle characteristics in the flow stream.

FIG. 23 is a schematic diagram showing an illustrative optical detection system that includes a polarizing beamsplitter 820, which may help provide further information regarding particles and/or particle characteristics in the flow stream. A flow channel is shown at 810. The flow channel has flow stream with one or more particles therein. A light source (not explicitly shown) directs a polarized input light beam 801 at the particles in the flow stream. In the illustrative embodiment, the polarized input light beam 801 has a polarization orientation that is into the page. In some embodiments, however, the polarized input light beam 801 may have two or more polarization orientations, if desired. Also, the polarized input light beam 801 is shown having an incident angle 803 that is about 45 degrees relative to the flow channel 810, although this is not required in all embodiments.

The polarized input light beam 801 interacts with one or more particles in the flow stream, and the particles provide an output light beam 802. A polarizing beamsplitter 820 is positioned to receiving at least part of the output light beam 801. The polarizing beamsplitter 820 may receive light scattered by one or more particles in the flow stream, or fluorescent light emitted from markers or tags, as described above.

In the illustrative embodiment the polarizing beamsplitter 820 receives the light that is scattered at an angle of about 90 degrees relative to the polarized input light beam 801, but this is not required in all embodiments. Some of the particles in the flow channel 810 may cause the output light beam 801 to have both a polarized and depolarized component. The polarized component may, for example, have a polarization orientation that is into the page, and the depolarized component may have a polarization orientation that is in the plane of the page. The polarizing beamsplitter 820 receives the output light beam 801 and provides a polarized light beam 812 and a depolarized light beam 814. The polarizing beamsplitter 820 may be, for example, a Wollaston prism in a cube (as shown in FIG. 23) or film form that provides an angle 840 between the polarized light beam 812 and the depolarized light beam 814 of less than 90 degrees or less, as shown.

A pair of photodetectors 832 and 834 may be provided for receiving the polarized light beam 812 and the depolarized light beam 814, respectively. In the example shown, photodetector 832 may provide a first output signal that corresponds to the polarized light beam 812, and photodetector 834 may provide a second output signal that corresponds to the depolarized light beam 814. A controller or processor may use the first output signal and the second output signal to help identify particles and/or particle characteristics in the flow channel 810. The data collected by the detectors 832 and 834 may, for example, help count and/or classify certain types of white blood cells such as eosinophils.

As noted above, and in some embodiments, the angle 840 between the polarized light beam 812 and the depolarized light beam 814 may be less than 90 degrees, and in some cases, less than 60 degrees, less than 30 degrees, less than 20 degrees, less than 10 degrees, or less than 5 degrees, as desired. When the angle 840 is less than 90 degrees, the spacing between the photodetectors 832 and 834 may be less than when a conventional polarizing beam splitter cube is used. In some cases, this may reduce the overall size of the device, and in some cases, may allow the photodetectors 832 and 834 to be placed on a common substrate with a reduced spacing.

Although the invention has been described with respect to at least one illustrative example, many variations and modifications will become apparent to those skilled in the art upon reading the present specification. It is therefore the intention that the appended claims be interpreted as broadly as possible in view of the prior art to include all such variations and modifications.

What is claimed is:

1. A cytometer for analyzing predetermined characteristics of biological particles within a flow stream, the cytometer comprising:
    a removable flow cytometry cartridge for receiving a sample fluid including biological particles and for hydrodynamic focusing the biological particles into a single file arrangement through an interrogation channel within the removable cartridge, the removable cartridge having a first sidewall with a first optically transparent window in optical communication with the interrogation channel, and a second sidewall opposite to the first sidewall with a second optically transparent window in optical communication with the interrogation channel;
    a housing for removably receiving the removable flow cytometry cartridge, the housing including:
        a light source for providing an input light beam to the interrogation channel through the first optically transparent window of the removable flow cytometry cartridge, the input light beam having a polarization direction;
        a polarizing beamsplitter for receiving an output light beam from the interrogation channel through the second optically transparent window of the removable flow cytometry cartridge, and for providing a polarized light beam and a depolarized light beam, wherein the polarized light beam and the depolarized light beam form an angle therebetween of less than 90 degrees; and
        light receiving means for receiving the polarized light beam and the depolarized light beam, and for providing a first output signal that corresponds to the polarized light beam and a second output signal that corresponds to the depolarized light beam.

2. The cytometer of claim 1 wherein the output light beam includes scattered light, and the polarizing beamsplitter receives a portion of the output light beam that is scattered in a direction that is about 90 degrees offset relative to the input light beam.

3. The cytometer of claim 2 wherein the polarizing beamsplitter includes a Wollaston prism.

4. The cytometer of claim 1 wherein the angle formed between the polarized light beam and the depolarized light beam is less than 20 degrees.

5. The cytometer of claim 1 wherein the angle formed between the polarized light beam and the depolarized light beam is less than 10 degrees.

6. The cytometer of claim 1 wherein the polarizing beamsplitter is a polarizing beamsplitter cube.

7. The cytometer of claim 1 wherein the polarizing beamsplitter is a polarizing beamsplitter film.

8. The cytometer of claim 1 wherein the light receiving means includes a pair of photodetectors.

9. The cytometer of claim 1 wherein the input light beam is polarized, and the polarized light beam has the same polarization as the input light beam.

10. The cytometer of claim 9 wherein the depolarized light beam has a polarization that is orthogonal to the polarization of the input light beam.

11. The cytometer of claim 1, further comprising processing means, the processing means using the first output signal and the second output signal to help classify the biological particles, wherein the biological particles include white blood cells.

12. The cytometer of claim 11, wherein the white blood cells include eosinophils.

13. The cytometer of claim 1, wherein the removable cartridge further includes a micro lens situated in optical communication with the first optically transparent window.

14. The cytometer of claim 1, wherein the removable cartridge further includes a micro lens situated in optical communication with the second optically transparent window.

15. A method for analyzing predetermined characteristics of biological particles within a flow stream within a fluidic cartridge that is removable received by a housing, the method comprising:
    inserting the fluidic cartridge into the housing;
    hydrodynamic focusing the biological particles into a single file arrangement through an interrogation channel within the fluidic cartridge;
    providing an input light beam from one or more light sources of the housing to the interrogation channel of the fluidic cartridge through a micro lens situated on the fluidic cartridge adjacent to a first side of the interrogation channel, the input light beam being provided at an angle of incidence of less than 90 degrees relative to the interrogation channel, the input light beam having a polarization direction;

receiving an output light beam from a second opposing side of the interrogation channel by a polarizing beamsplitter, the polarizing beamsplitter producing a polarized light beam and a depolarized light beam, wherein the polarized light beam and the depolarized light beam form an angle therebetween of less than 90 degrees;

detecting the polarized light beam and the depolarized light beam, and providing a first output signal that corresponds to the polarized light beam and a second output signal that corresponds to the depolarized light beam; and removing the fluidic cartridge from the housing.

16. The method of claim 15 wherein the output light beam that is provided to the polarizing beamsplitter is scattered about 90 degrees relative to the input light beam by the flow stream.

17. The method of claim 15 wherein the angle formed between the polarized light beam and the depolarized light beam is less than 20 degrees.

18. The method of claim 15 wherein the angle formed between the polarized light beam and the depolarized light beam is less than 10 degrees.

19. The method of claim 15 wherein the polarizing beamsplitter is a polarizing beamsplitter cube.

20. The method of claim 15 wherein the polarizing beamsplitter is a polarizing beamsplitter film.

21. The method of claim 15 wherein the polarizing beamsplitter includes a Wollaston prism.

22. The method of claim 15 wherein the polarized light beam and the depolarized light beam are detected using a pair of photodetectors.

23. The method of claim 15 wherein the polarized light beam has the same polarization as the input light beam.

24. The method of claim 15 wherein the depolarized light beam has a polarization that is orthogonal to the polarization of the input light beam.

25. An optical detection system for analyzing predetermined characteristics of biological particles in a flow stream, the optical detection system comprising:

a removable cartridge for receiving a sample fluid including biological particles and for hydrodynamic focusing the biological particles into a single file arrangement through an interrogation channel of the removable cartridge, the removable cartridge having a first sidewall with a first optically transparent window in optical communication with the interrogation channel, and a second sidewall opposite to the first sidewall with a second optically transparent window in optical communication with the interrogation channel;

a housing for removably receiving the removable cartridge, the housing including:
    a light source for providing an input light beam to the interrogation channel through the first optically transparent window of the removable cartridge, the input light beam having in incident angle relative to the interrogation channel and a polarization direction;
    a polarizing beamsplitter configured to receive an output light beam from the interrogation channel through the second optically transparent window of the removable cartridge, the output light beam exiting about 90 degrees relative to the incident angle of the input light beam, the polarizing beamsplitter providing a polarized light beam and a depolarized light beam, wherein the polarized light beam and the depolarized light beam form an angle therebetween of less than 90 degrees;
    the second optically transparent window of the removable cartridge having a filter for at least partially filtering out the input light beam from exiting with the output light beam; and
    light receiving means for receiving the polarized light beam and the depolarized light beam, and for providing a first output signal that corresponds to the polarized light beam and a second output signal that corresponds to the depolarized light beam.

26. The optical detection system of claim 25 wherein the polarized light beam has the same polarization as the input light beam.

27. The optical detection system of claim 26 wherein the depolarized light beam has a polarization that is orthogonal to the polarization of the input light beam.

28. The optical detection system of claim 25, wherein the first optically transparent window of the removable cartridge includes a micro lens for receiving the input light beam.

29. The optical detection system of claim 25, wherein the second optically transparent window of the removable cartridge includes a micro lens for modifying the output light beam.

30. The optical detection system of claim 28, wherein the second optically transparent window of the removable cartridge includes a micro lens for modifying the output light beam.

* * * * *